United States Patent
Tang et al.

(10) Patent No.: US 12,275,961 B2
(45) Date of Patent: *Apr. 15, 2025

(54) METHOD FOR UTILIZING ENGINEERED DENDRITIC CELLS TO INDUCE GUT-HOMING REGULATORY T CELLS AND TREAT GUT INFLAMMATION

(71) Applicant: LOMA LINDA UNIVERSITY, Loma Linda, CA (US)

(72) Inventors: Xiaolei Tang, Loma Linda, CA (US); David J. Baylink, Redlands, CA (US); K.-H. William Lau, Redlands, CA (US); Michael Walter, Loma Linda, CA (US)

(73) Assignee: LOMA LINDA UNIVERSITY, Loma Linda, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 16/744,296

(22) Filed: Jan. 16, 2020

(65) Prior Publication Data
US 2020/0149121 A1 May 14, 2020

Related U.S. Application Data

(63) Continuation of application No. 15/550,501, filed as application No. PCT/US2016/017610 on Feb. 11, 2016, now Pat. No. 10,577,669.

(60) Provisional application No. 62/115,040, filed on Feb. 11, 2015.

(51) Int. Cl.
| | |
|---|---|
| *C12N 5/0784* | (2010.01) |
| *A61K 38/44* | (2006.01) |
| *A61K 39/00* | (2006.01) |
| *A61K 48/00* | (2006.01) |
| *C12N 9/02* | (2006.01) |
| *C12P 19/34* | (2006.01) |

(52) U.S. Cl.
CPC ............ *C12N 9/0008* (2013.01); *A61K 38/44* (2013.01); *A61K 39/4615* (2023.05); *A61K 39/4621* (2023.05); *A61K 39/4622* (2023.05); *A61K 39/46433* (2023.05); *A61K 39/464454* (2023.05); *A61K 48/00* (2013.01); *C12N 9/0073* (2013.01); *C12P 19/34* (2013.01); *C12Y 102/01036* (2013.01); *C12Y 114/13013* (2013.01); *A61K 2239/31* (2023.05); *A61K 2239/38* (2023.05)

(58) Field of Classification Search
None
See application file for complete search history.

(56) References Cited

U.S. PATENT DOCUMENTS

| | | |
|---|---|---|
| 6,274,359 B1 | 8/2001 | Anazawa et al. |
| 8,530,153 B1 | 9/2013 | Kung |
| 8,647,616 B2 | 2/2014 | Baylink et al. |
| 8,669,104 B1 | 3/2014 | Baylink et al. |
| 8,722,399 B1 | 5/2014 | Baylink et al. |
| 2006/0263340 A1 | 11/2006 | Andrian et al. |
| 2007/0031396 A1 | 2/2007 | Maden et al. |
| 2010/0273748 A1 | 10/2010 | Gallo et al. |
| 2014/0141005 A1 | 5/2014 | Baylink et al. |
| 2018/0030553 A1 | 2/2018 | Tang et al. |

FOREIGN PATENT DOCUMENTS

| | | |
|---|---|---|
| WO | 2002062820 | 8/2002 |
| WO | 2016130845 | 8/2016 |

OTHER PUBLICATIONS

Hewison et al., Extra-renal 25-hydroxyvitamin D3-1alpha hydroxylase in human health and disease, Journal of Steroid Biochemistry & Molecular Biology, Mar. 15, 2007, vol. 103, pp. 316-321.

Charrier et al., Lentiviral vectors targeting WASp expression to hematopoietic cells, efficiently transduce and correct cells from WAS patients, Gene Therapy, Oct. 19, 2006, vol. 14, pp. 415-428.

International Search Report and Written Opinion for PCT/US2016/017610, Apr. 22, 2016.

*Primary Examiner* — Michael D Burkhart
(74) *Attorney, Agent, or Firm* — Womble Bond Dickinson (US) LLP

(57) ABSTRACT

Gene-modified, lymphoid-tissue-homing dendritic cells that comprise a 1-alpha-hydroxylase gene and a retinaldehyde dehydrogenase 2 gene, where the 1-alpha-hydroxylase gene is expressed to produce functional 1-alpha-hydroxylase enzyme and the retinaldehyde dehydrogenase 2 gene is expressed to produce functional retinaldehyde dehydrogenase 2 gene enzyme. A method for treating one or more than one inflammation-related condition or disease, the method comprising administering gene-modified, lymphoid-tissue-homing dendritic cells that comprise a 1-alpha-hydroxylase gene and a retinaldehyde dehydrogenase 2 gene, where the 1-alpha-hydroxylase gene is expressed to produce functional 1-alpha-hydroxylase enzyme and the retinaldehyde dehydrogenase 2 gene is expressed to produce functional retinaldehyde dehydrogenase 2 gene enzyme.

10 Claims, 10 Drawing Sheets

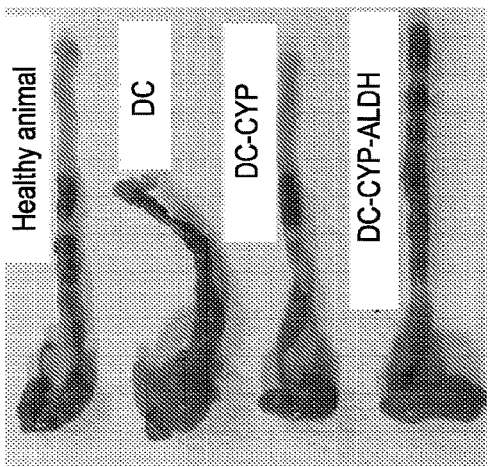
FIG. 3C
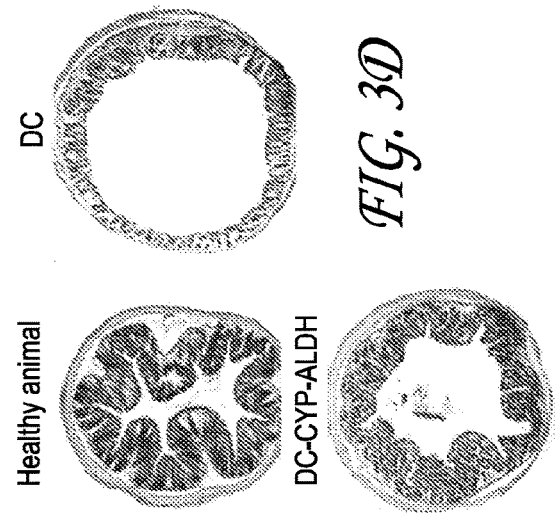
FIG. 3D
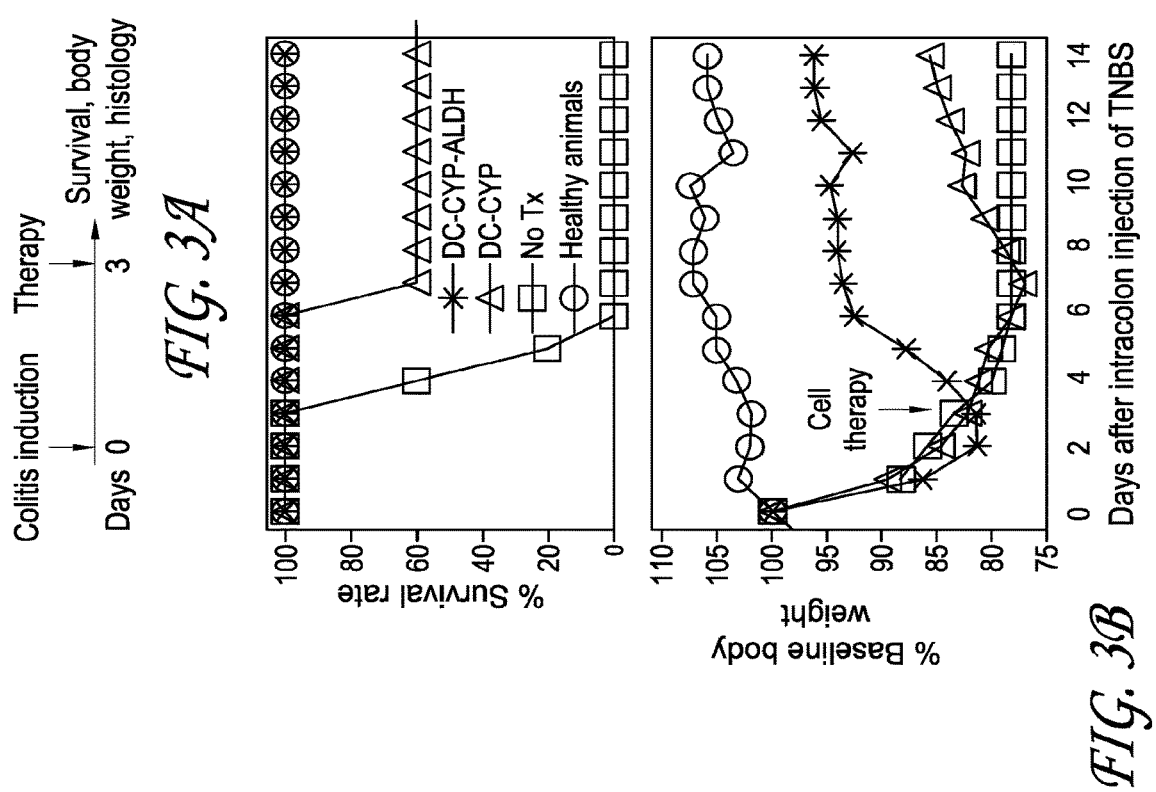
FIG. 3A
FIG. 3B

METHOD FOR UTILIZING ENGINEERED DENDRITIC CELLS TO INDUCE GUT-HOMING REGULATORY T CELLS AND TREAT GUT INFLAMMATION

CROSS-REFERENCE TO RELATED APPLICATIONS

This application is a continuation, and claims priority to and the benefit of U.S. Non-Provisional application Ser. No. 15/550,501, filed Aug. 11, 2017, titled "A METHOD FOR UTILIZING ENGINEERED DENDRITIC CELLS TO INDUCE GUT-HOMING REGULATORY T CELLS AND TREAT GUT INFLAMMATION," which is U.S. national stage entry under 35 U.S.C. § 371 of International Application No. PCT/US2016/017610, filed Feb. 11, 2016, titled "A METHOD FOR UTILIZING ENGINEERED DENDRITIC CELLS TO INDUCE GUT-HOMING REGULATORY T CELLS AND TREAT GUT INFLAMMATION" which claims priority to U.S. Provisional Application No. 62/115,040, filed Feb. 11, 2015, titled "METHOD FOR UTILIZING ENGINEERED DENDRITIC CELLS TO INDUCE GUT-HOMING REGULATORY T CELLS AND TREAT GUT INFLAMMATION," the full disclosure of which is hereby incorporated herein by reference in its entirety.

GOVERNMENT SUPPORT

This invention was made with government support under grant number: W81XWH-15-1-0240 awarded by Defense Health Agency Medical Research and Development Branch. The government has certain rights in the invention.

BACKGROUND

Inflammation is the usual initial response of the body to harmful stimuli and is necessary for the healing of most diseases and conditions. Both the initiation of inflammation and the cessation of inflammation are complex processes. It is now known that many human conditions and diseases are caused by the inappropriate initiation of inflammation or the inappropriate lack of cessation of inflammation. Some of these 'inflammation-related conditions and diseases' involve simultaneous inflammation of many body tissues or organs such as for example sepsis and polytrauma. Others involve inflammation limited to specific body tissues or organs such as for example inflammatory neurodegenerative diseases [e.g. Alzheimer's disease] and autoimmune diseases [e.g. antiphospholipid syndrome, atherosclerosis, autoimmune encephalomyelitis, autoimmune hepatitis, celiac disease, Graves' disease, inflammatory bowel disease (Crohn's disease and ulcerative colitis), multiple sclerosis, myasthenia gravis, myositis, polymyositis, Raynaud's phenomenon, rheumatoid arthritis, scleroderma, Sjogren's syndrome, systemic lupus, type 1 diabetes and uveitis].

Treatment of inflammation-related conditions and diseases include the administration of therapeutic agents to reduce or cease inflammation, such as anti-inflammatory agents (including 5-aminosalicylates and corticosteroids), biological drugs (including infliximab and vizilizumab) and immunosuppressants (including azathioprine, cyclosporine and mercaptopurine). Disadvantageously, however, these therapeutic agents can have severe side effects including increased risks for infectious diseases, malignancies and osteoporosis. Further, many patients do not respond to these therapeutic agents. Additionally, many of these therapeutic agents do not provide long term efficacy.

Therefore, there is a need for a new method for treating inflammation-related conditions and diseases which is not associated with these disadvantages.

SUMMARY

Methods and compositions for the treatment or prevention of intestinal (the GUT) inflammation and pain are provided.

According to one embodiment, a gene-modified dendritic cell suitable for treating one or more than one inflammation-related conditions or diseases; the gene-modified dendritic cell comprising a 1-alpha-hydroxylase gene that produces functional 1-alpha-hydroxylase and a retinaldehyde dehydrogenase 2 gene that produces functional retinaldehyde dehydrogenase 2 (RALDH2). In some embodiments, wherein the gene-modified, dendritic cell is administered to a patient. In some embodiments, the gene-modified, dendritic cell wherein after administration to the patient the gene-modified, dendritic cell migrates into and actively produce 1,25(OH)2D and retinoic acid (RA) in peripheral lymphoid organs.

According to another embodiment, a pharmaceutical suitable for treating one or more than one inflammation-related conditions or diseases, the pharmaceutical comprising: a gene-modified, dendritic cell comprising a 1-alpha-hydroxylase gene that produces functional 1-alpha-hydroxylase and a retinaldehyde dehydrogenase 2 gene that produces functional retinaldehyde dehydrogenase 2.

According to another embodiment, a method for treating one or more than one inflammation-related conditions or diseases, the method comprises: identifying a patient with an inflammation-related condition or disease, where the inflammation-related condition or disease is caused by the inappropriate initiation of inflammation or the inappropriate lack of cessation of inflammation; obtaining dendritic cells; producing gene-modified dendritic cells, where the gene-modified dendritic cells comprise a 1-alpha-hydroxylase gene, where the 1-alpha-hydroxylase gene is expressed to produce functional 1-alpha-hydroxylase enzyme and a retinaldehyde dehydrogenase 2 gene, where the retinaldehyde dehydrogenase 2 gene is expressed to produce functional retinaldehyde dehydrogenase 2; administering an amount of the gene-modified dendritic cells to the patient; allowing the gene-modified dendritic cells to locate and enter into the inflamed organ or tissue affected by the condition or disease; and allowing the production of 1-alpha-hydroxylase and retinaldehyde dehydrogenase 2.

According to another embodiment, a vector for generating a gene-modified dendritic cell suitable for treating one or more than one inflammation-related condition or disease, the vector can comprise a vector backbone; a 1-alpha-hydroxylase gene that produces functional 1-alpha-hydroxylase and a retinaldehyde dehydrogenase 2 gene that produces functional retinaldehyde dehydrogenase 2; a SSFV promotor and a PGK promotor, wherein the SSFV promotor controls the expression of the 1-alpha-hydroxylase gene and the PGK promotor controls the expression of the retinaldehyde dehydrogenase 2 gene. In some embodiments, the vector wherein the vector comprises a lentiviral or human applicable (e.g. AAV) vector. In some embodiments, the vector wherein the vector is packaged into a viral particle. In some embodiments, the vector wherein bone-marrow- or PBMC (peripheral blood mononuclear cells)-derived dendritic cells are transduced with the vector thereby generating the gene-modified dendritic cell. In some embodiments, the vector wherein the gene-modified dendritic cell is administered to a patient. In some embodiments, the vector wherein after administration to the patient the gene-modified dendritic cell migrates into and actively produce 1,25(OH)2D and retinoid acid in peripheral lymphoid organs.

BRIEF DESCRIPTION OF THE DRAWINGS

FIG. 2A is a representative microscope image showing a typical phenotype of myeloid DCs (i.e. protruding dendrites) of cultured DCs.

FIG. 2B is a representative FACS plot showing that 90.5% of cultured DCs expressed a DC marker, i.e. CD11c FIG. 2C is a representative FACS plot showing comparing expression of 1α-hydroxylase in DC-CYP-ALDH cells to non-engineered DCs.

FIG. 2D depicts data showing the production of 1,25[OH]$_2$D in DC-CYP and DC-CYP-ALDH cultures as compared to non-engineered DCs and DC-ALDH cultures.

FIG. 2E depicts a representative FACS plot showing RALDH activity in the DC-CYP-ALDH cells as compared to non-engineered DCs.

FIG. 3A depicts an experimental design for testing whether cells constitutively overexpressing 1α-hydroxylase and RALDH2 rapidly arrest the progression of ongoing experimental colitis.

FIG. 3B depicts the survival rate and body weight of mice in an experiment run using the method of FIG. 3A.

FIG. 3C depicts representative images of colon lengths from an experiment run using the method of FIG. 3A.

FIG. 3D depicts H&E staining of colons from an experiment run using the method of FIG. 3A.

DETAILED DESCRIPTION OF THE PREFERRED EMBODIMENT

Figure 1:
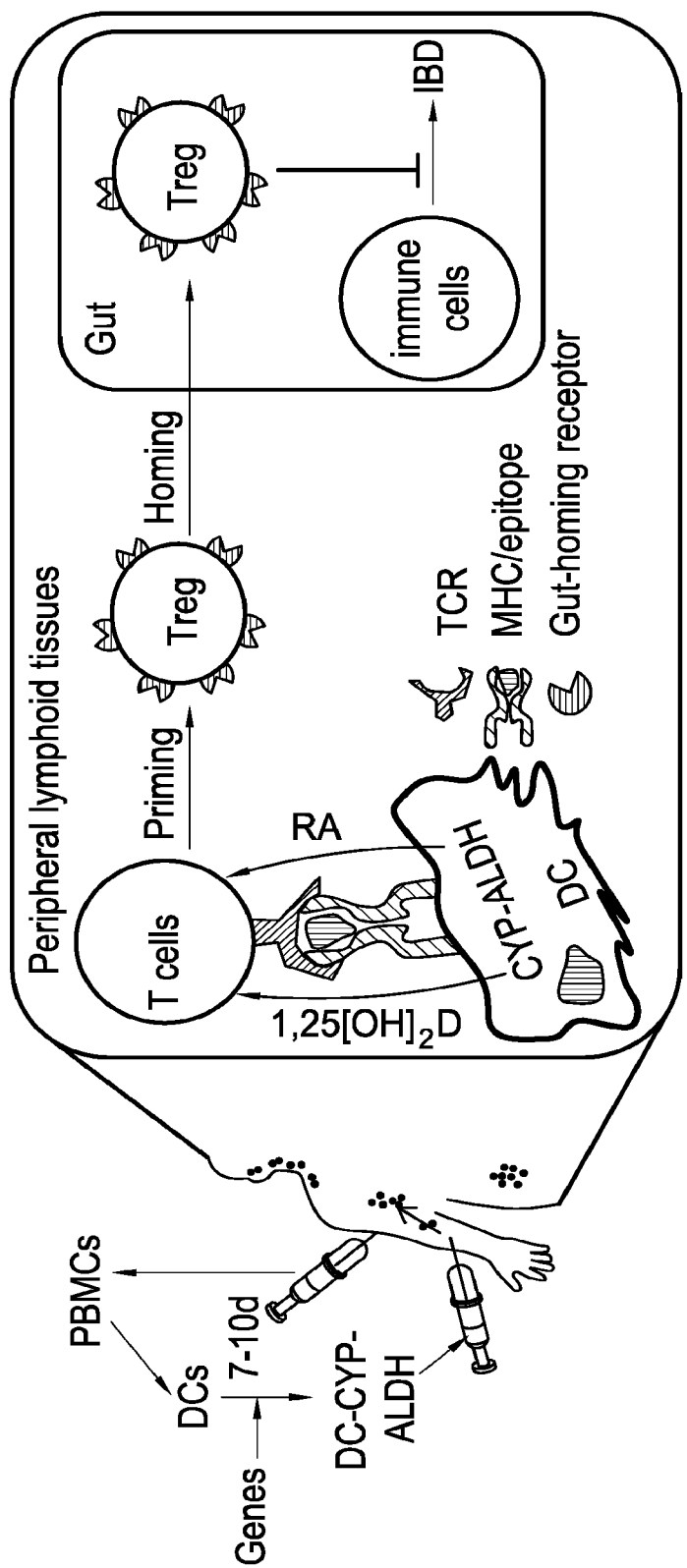
FIG. 1 depicts a schematic representation of an embodiment of programming of gut-homing Treg cells to reduce the symptoms of IBD.

The present disclosure is generally related to the use of genetically modified dendritic cells to treat inflammatory conditions. More particularly, lymphoid-tissue-homing dendritic cells are engineered to comprising at least one of a 1-alpha-hydroxylase gene that produces functional 1-alpha-hydroxylase and a retinaldehyde dehydrogenase 2 gene that produces functional retinaldehyde dehydrogenase 2. In some embodiments, lymphoid-tissue-homing dendritic cells are engineered to overexpress a 1-alpha-hydroxylase gene that produces functional 1-alpha-hydroxylase and a retinaldehyde dehydrogenase 2 gene that produces functional retinaldehyde dehydrogenase 2. Expression levels may be controlled, turned on/off, and/or modified using known expression constructs and methods.

Lymphoid-tissue-homing dendritic cells as used herein can refer to dendritic cells produced from either bone marrow or peripheral blood monocytes per standard protocol and widely used in animal studies and in human clinical trials. The dendritic cells have the capacity to home to peripheral lymphoid tissues. The dendritic cells have the capacity to home to peripheral lymphoid tissues upon in vivo injection and do not need any treatment to gain the lymphoid-tissue-homing property. These DCs can be engineered for overexpression of the 1α-hydroxylase and RALDH2 such that the engineered DCs will migrate into the peripheral lymphoid tissues to induce gut-homing regulatory T (Treg) cells. For example, an amount of the gene-modified, lymphoid-tissue-homing dendritic cells can be administered to a patient, allowing the gene-modified, lymphoid-tissue-homing dendritic cells to locate, enter into, and produce 1-alpha-hydroxylase and retinaldehyde dehydrogenase 2 in the peripheral lymphoid tissues to induce gut-homing regulatory T (Treg) cells, wherein the gut-homing Treg cells locate and enter into the inflamed GUT affected by the condition or disease.

One therapeutic agent known to be effective in the treatment of inflammation-related conditions and diseases is calcitriol, the active form of vitamin D that is partially responsible for the regulation of calcium levels in humans. While the systemic administration of calcitriol has been shown to be effective in treatment of various autoimmune inflammation-related conditions and diseases in animal models, disadvantageously, the dosage of calcitriol needed to be effective was high enough to cause hypercalcemia in the treated animal limiting the potential use of calcitriol as a therapeutic agent. Further, there is evidence that deficient levels of calcitriol is a significant factor to the pathogenesis of sepsis in that there is evidence that an impairment of the production of calcitriol is associated with low serum calcium and high parathyroid hormone, and there is evidence polytrauma is frequently associated with hypocalcemia and increasing parathyroid hormone, which could also be related to impaired vitamin D metabolism.

Some of the molecular approaches to engineering dendritic cells and treating conditions for which 1-alpha-hydroxylase and/or retinaldehyde dehydrogenase 2 may be beneficial are disclosed in U.S. Pat. No. 8,647,616 (U.S. application Ser. No. 13/766,733 filed Feb. 13, 2013), U.S. Pat. No. 8,669,104 (U.S. application Ser. No. 14/076,055 filed Nov. 8, 2013), and U.S. Pat. No. 8,722,399 (U.S. application Ser. No. 14/163,933 filed Jan. 24, 2014) incorporated herein in its entirety, which teaches engineering of inflammation-specific macrophages to comprise a 1-alpha-hydroxylase gene that produces functional 1-alpha-hydroxylase. Accordingly, some of the embodiments, definitions and methodology disclosed in U.S. Pat. Nos. 8,647,616, 8,669, 104, and 8,722,399 are included in the present disclosure.

According to one embodiment, there is provided gene-modified, inflammation-specific monocytes suitable for treating one or more than one inflammation-related condition or disease. According to another embodiment, there is provided gene-modified, inflammation-specific macrophages suitable for treating one or more than one inflammation-related condition or disease. In one embodiment, the gene-modified, inflammation-specific macrophages are produced by transdifferentiation of gene-modified, inflammation-specific monocytes. According to another embodiment, there is provided a pharmaceutical suitable for treating inflammation-related conditions and diseases. The pharmaceutical comprises gene-modified, inflammation-specific monocytes according to the present invention or comprises gene-modified, inflammation-specific macrophages. According to one embodiment, there provided a method for treating one or more than one inflammation-related condition or disease. The method comprises generating calcitriol directly within the organ or tissue affected by the inflammation-related condition or disease by causing expression of the gene for the enzyme 1-alpha-hydroxylase, the rate-limiting step in humans for synthesizing calcitriol, to the affected organ or tissue using gene-modified, inflammation-specific monocytes that specifically home to sites of inflammation. The calcitriol that is generated suppresses the inflammation by regulating the development and function of cell types involved in producing the inflammation. In a preferred embodiment, the method comprises adoptive transfer of gene-modified, inflammation-specific monocytes that overexpress the 1-alpha-hydroxylase gene and that are controlled by a promoter that limits expression of the 1-alpha-hydroxylase gene to the inflamed organ or tissue. Generating calcitriol directly within the inflamed organ or tissue advantageously decreases the systemic side effects of direct calcitriol administration, including eliminating systemic hypercalcemia associated with present methods of systemic administration of calcitriol directly. The monocytes, macrophages, pharmaceuticals and method will now be disclosed in detail.

The agents and methods describe in detail the use of inflammation-specific monocytes comprising a 1-alpha-hydroxylase gene. In other embodiments, the agents and methods described with reference to monocytes and macrophages and pharmaceuticals and methods thereof has been applied to other systems including for dendritic cells (DCs), a subset of immune cells, for expression of both 1α hydroxylase and retinaldehyde dehydrogenase 2 (RALDH2).

As used in this disclosure, except where the context requires otherwise, the term "comprise" and variations of the term, such as "comprising," "comprises" and "comprised" are not intended to exclude other additives, components, integers or steps.

As used in this disclosure, except where the context requires otherwise, the method steps disclosed are not intended to be limiting nor are they intended to indicate that each step is essential to the method or that each step must occur in the order disclosed.

As used in this disclosure, except where the context requires otherwise, "tissue" includes both one histological type of tissue, as well as a plurality of histological types of tissue forming an organ or organ system, such as for example 'pancreatic tissue,' 'Gut tissues', 'brain tissue', as will be understood by those with skill in the art.

As used in this disclosure, "calcidiol" means (6R)-6-[(1R, 3aR,4E,7aR)-4-[(2Z)-2-[(5 S)-5-Hydroxy-2-methylidene-cyclohexylidene]ethylidene]-7a-methyl-,3,3a,5,6,7-hexahydro-1H-inden-1-yl]-2-methyl-heptan-2-ol (also known as vitamin D2, 25-hydroxycholecalciferol; 25-hydroxyvitamin D3; 25(OH)D; 25(OH)D2; 25(OH)D3; and calcifediol, among other names.

As used in this disclosure, "calcitriol" means (1R,3S)-5-[2-[(1R,3aR,7aS)-1-[(2R)-6-hydroxy-6-methyl-heptan-2-yl]-7a-methyl-2,3,3a, 5,6,7-hexahydro-1H-inden-4-ylidene]ethylidene]-4-methylidene-cyclohexane-1,3-diol (also known as vitamin D3; 1,25-dihydroxyvitamin D; 1,25-dihydroxyvitamin D2; 1,25-dihydroxyvitamin D3; 1,25-dihydroxycholecalciferol; 1,25(OH)2D; 1,25(OH)2D2; and 1,25(OH)2D3), among other names.

As used in this disclosure, "1-alpha-hydroxylase gene" encodes the enzyme 1-alpha-hydroxylase, also known under the following alternate names and forms: calcidiol 1-monooxygenase; CYP1 alpha; CYP27B1; CP2B; CYP27B; cytochrome P450VD1-alpha; cytochrome p450 27B1; cytochrome P450, family 27, subfamily B, polypeptide 1; cytochrome P450 subfamily XXVIIB polypeptide 1; cytochrome P450, subfamily XXVIIB (25-hydroxyvitamin D-1-alpha-hydroxylase), polypeptide 1; cytochrome p450 27B1; cytochrome P450C1 alpha; cytochrome P450 VD1-alpha; cytochrome P450 27B1; 1alpha(OH)ase2; 25-hydroxyvitamin D-1 alpha hydroxylase, mitochondrial; 25 hydroxyvitamin D3-1-alpha hydroxylase2; 25-hydroxyvitamin D(3) 1-alpha-hydroxylase; and 25-OHD-1 alpha-hydroxylase; and VD1 hydroxylase, among other names.

As used in this disclosure, the enzyme "1-alpha-hydroxylase" catalyzes the hydroxylation of "calcidiol" to "calcitriol" which is the rate-limiting step in the production of calcitriol in humans.

As used in this disclosure, "inflammation-related" in connection with "condition or disease" or "conditions and diseases" means "caused by the inappropriate initiation of inflammation or the inappropriate lack of cessation of inflammation" rather than merely associated with inflammation.

As used in this disclosure, "inflammation-specific monocytes" are monocytes that home specifically to inflamed tissues.

As used in this disclosure, "inflammation-specific macrophages" are macrophages that home specifically to inflamed tissues.

As used in this disclosure, "GFP" means green fluorescent protein.

In some embodiments, the methods described herein can be used to treat inflammatory bowel diseases (IBDs); however, it may be applicable to the therapies of other inflammatory diseases in the intestines as well. IBDs are a group of diseases that are conditions of chronic inflammation in the gastrointestinal tract. According to CDC, as many as 1.4 million persons in the United States are suffering from IBDs. The two common forms of IBDs are ulcerative colitis (UC) and Crohn's disease (CD). IBDs display high morbidity and are often associated with extraintestinal manifestations (EIMs), e.g. colorectal carcinoma and low bone mineral density among others.

There is so far no cure for IBDs. Current therapeutic goals of IBD treatment are to induce remission (periods of times that are symptom-free), maintain remission (prevention of disease flare-ups), and improve patients' life quality. During the current treatments, one-quarter to one-third of patients with UC and two-thirds to three-quarters of patients with CD still require surgery. Thus, there are unmet therapeutic needs for IBDs.

Agents and Method for Treating Inflammation-Related Conditions and Diseases

According to one embodiment, there is provided gene-modified, inflammation-specific monocytes suitable for treating one or more than one inflammation-related conditions or diseases. The gene-modified, inflammation-specific monocytes comprise any of the gene-modified, inflammation-specific monocytes disclosed for use in the present methods. The gene-modified, inflammation-specific monocytes comprise a 1-alpha-hydroxylase gene that produces functional 1-alpha-hydroxylase when the monocytes transdifferentiate into gene-modified, inflammation-specific macrophages. In a preferred embodiment, the 1-alpha-hydroxylase gene is a human 1-alpha-hydroxylase gene. In one embodiment, the 1-alpha-hydroxylase gene is on plasmid DNA. In another embodiment, the 1-alpha-hydroxylase gene is on a viral vector. In a preferred embodiment, the gene-modified, inflammation-specific monocytes further comprise a growth factor gene that produces functional growth factor when the gene-modified, inflammation-specific monocytes transdifferentiate into gene-modified, inflammation-specific macrophages. In one embodiment, the growth factor gene is a human growth factor gene. In one embodiment, the growth factor gene is on plasmid DNA. In another embodiment, the growth factor gene is on a viral vector. In one embodiment, the growth factor gene is selected from the group consisting of insulin-like growth factor 1 (IGF-1) (also known as somatomedin C) and a transforming growth factor beta gene (TGF-β); however, other growth factor genes can be used, as will be understood by those with skill in the art with respect to this disclosure. In another preferred embodiment, the gene-modified, inflammation-specific monocytes further comprise a macrophage-specific promoter that limits expression of the 1-alpha-hydroxylase gene until the gene-modified, inflammation-specific monocytes transdifferentiate into gene-modified, inflammation-specific macrophages. In one embodiment, the macrophage-specific promoter is selected from the group consisting of CD11b (Mac-1), CD14, c-fms, Lysozyme M and Scavenger Receptor Class A (SRA). In a particularly preferred embodiment, the gene-modified, inflammation-specific monocytes comprise a 1-alpha-hydroxylase gene that produces functional 1-alpha-hydroxylase when the gene-modified, inflammation-specific monocytes transdifferentiate into gene-modified, inflammation-specific macrophages, and further comprise a growth factor gene that produces functional growth factor when the gene-modified, inflammation-specific monocytes transdifferentiate into gene-modified, inflammation-specific macrophages, and further comprises a macrophage-specific promoter that limits expression of the 1-alpha-hydroxylase gene until the gene-modified, inflammation-specific monocytes transdifferentiate into gene-modified, inflammation-specific macrophages. In one embodiment, the gene-modified, inflammation-specific monocytes are CD14-positive and CD16-negative (+CD16−; CD14+CD16−) monocytes.

According to one embodiment of the present invention, there is provided gene-modified, inflammation-specific macrophages suitable for treating one or more than one inflammation-related conditions or diseases. The gene-modified, inflammation-specific macrophages comprise any of the gene-modified, inflammation-specific macrophages disclosed for use in the present method. In one embodiment, the gene-modified, inflammation-specific macrophages have transdifferentiated from gene-modified, inflammation-specific monocytes according to the present invention. The gene-modified, inflammation-specific macrophages comprise a 1-alpha-hydroxylase gene that produces functional 1-alpha-hydroxylase. In a preferred embodiment, the 1-alpha-hydroxylase gene is a human 1-alpha-hydroxylase gene. In one embodiment, the 1-alpha-hydroxylase gene is on plasmid DNA. In another embodiment, the 1-alpha-hydroxylase gene is on a viral vector. In a preferred embodiment, the gene-modified, inflammation-specific macrophages further comprise a growth factor gene that produces functional growth factor. In one embodiment, the growth factor gene is a human growth factor gene. In one embodiment, the growth factor gene is on plasmid DNA. In another embodiment, the growth factor gene is on a viral vector. In one embodiment, the growth factor gene is selected from the group consisting of insulin-like growth factor 1 (IGF-1) (also known as somatomedin C) and a transforming growth factor beta gene (TGF-β); however, other growth factor genes can be used, as will be understood by those with skill in the art with respect to this disclosure. In another preferred embodiment, the gene-modified, inflammation-specific macrophages further comprise a macrophage-specific promoter that limits expression of the 1-alpha-hydroxylase gene to macrophages. In one embodiment, the macrophage-specific promoter is selected from the group consisting of CD11b (Mac-1), CD14, c-fms, Lysozyme M and Scavenger Receptor Class A (SRA) CD14. In a particularly preferred embodiment, the gene-modified, inflammation-specific macrophages comprise a 1-alpha-hydroxylase gene that produces functional 1-alpha-hydroxylase, and further comprises a growth factor gene that produces functional growth factor, and further comprises a macrophage-specific promoter. In one embodiment, the gene-modified, inflammation-specific macrophages are M2 macrophages, such as for example M2 macrophages Type A, and M2 macrophages Type B. In another embodiment, the modified M2 macrophages are Gr1-positive M2 macrophages (Gr-1+ macrophages). In another embodiment, the gene-modified, inflammation-specific macrophages are Mac1-positive macrophages (Macrophage-1 antigen macrophages; integrin alphaMbeta2 macrophages).

According to another embodiment, there is provided a pharmaceutical suitable for treating one or more than one inflammation-related conditions or diseases. In one embodiment, the pharmaceutical comprises gene-modified, inflammation-specific monocytes. In another embodiment, the pharmaceutical comprises gene-modified, inflammation-specific macrophages according to the present invention. In another embodiment, the pharmaceutical comprises both gene-modified, inflammation-specific monocytes and comprises gene-modified, inflammation-specific macrophages. In one embodiment, the pharmaceutical comprises one or more than one substance selected from the group consisting of an anti-inflammatory agent (such as for example a 5-aminosalicylates and a corticosteroid), a cell growth media, an immunosuppressant (such as for example azathioprine, cyclosporine and mercaptopurine), a monoclonal antibody (such as for example infliximab and vizilizumab) and a preservative.

According to one embodiment, there is provided a method for treating one or more than one inflammation-related conditions or diseases. The method comprises, first, identifying a patient with an inflammation-related condition or disease suitable for treatment by the present method, where the inflammation-related condition or disease is caused by the inappropriate initiation of inflammation or the inappropriate lack of cessation of inflammation. In a preferred embodiment, the patient is a human. In one embodiment, the one or more than one inflammation-related condition or disease involves simultaneous inflammation of a plurality of body tissues or organs. In a preferred embodiment, the one or more than one inflammation-related condition or disease that involves simultaneous inflammation of a plurality of body tissues or organs is selected from the group consisting of sepsis and polytrauma. In a preferred embodiment, the one or more than one inflammation-related condition or disease lacks an autoimmune component. In a preferred embodiment, the one or more than one inflammation-related condition or disease that lacks an autoimmune component is selected from the group consisting of sepsis and polytrauma. In another embodiment, the one or more than one inflammation-related condition or disease involves inflammation limited to one specific body tissue or organ. In another embodiment, the one or more than one inflammation-related condition or disease is an autoimmune disease. In a preferred embodiment, the condition or disease is selected from the group consisting of Alzheimer's disease, antiphospholipid syndrome, atherosclerosis, autoimmune encephalomyelitis, autoimmune hepatitis, celiac disease, Graves' disease, inflammatory bowel disease (Crohn's disease and ulcerative colitis), multiple sclerosis, myasthenia gravis, myositis, polymyositis, Raynaud's phenomenon, rheumatoid arthritis, scleroderma, Sjogren's syndrome, systemic lupus, type 1 diabetes and uveitis. In one embodiment, identifying the patient comprises diagnosing the patient with one or more than one inflammation-related condition or disease suitable for treatment by the present method. In one embodiment, diagnosing the patient comprises performing one or more than one of action selected from the group consisting of performing a physical examination, performing a non-invasive imaging examination (such as for example computerized tomography, magnetic resonance imaging and ultrasound), and identifying one or more than one marker for the inflammation-related condition or disease in the blood or other body fluid of the patient. In another embodiment, identifying the patient comprises consulting patient records to determine if the patient has an inflammation-related condition or disease suitable for treatment by the present method.

Next, the method comprises obtaining inflammation-specific monocytes (ISMs). Inflammation-specific monocytes home to inflamed tissue, but not to uninflammed tissue. In one embodiment, the inflammation-specific monocytes are CD14-positive and CD16-negative (+CD16−; CD14+ CD16−) monocytes. In one embodiment, obtaining inflammation-specific monocytes (ISMs) comprises procuring embryonic stem cells, such as for example by isolating embryonic stem cells from fertilized eggs, and differentiating the embryonic stem cells into the inflammation-specific monocytes, as will be understood by those with skill in the art with respect to this disclosure. In another embodiment, obtaining inflammation-specific monocytes (ISMs) comprises extracting a body fluid or body tissue containing inflammation-specific monocytes (ISMs) from the patient. In one embodiment, extracting a body fluid or body tissue containing inflammation-specific monocytes from the patient comprises obtaining venous blood from the patient by performing venipuncture on the patient and extracting the inflammation-specific monocytes from the venous blood. In another embodiment, extracting a body fluid or body tissue containing inflammation-specific monocytes from the patient comprises performing adsorptive apheresis on the blood of the patient and extracting the inflammation-specific monocytes from the blood of the patient. In another preferred embodiment, extracting a body fluid or body tissue containing inflammation-specific monocytes from the patient comprises obtaining bone marrow from the patient by performing a bone marrow biopsy on the patient and extracting the inflammation-specific monocytes from the bone marrow of the patient. In another preferred embodiment, extracting a body fluid or body tissue containing inflammation-specific monocytes from the patient comprises obtaining preserved cord blood of the patient and extracting the inflammation-specific monocytes from the preserved cord blood. In another preferred embodiment, obtaining a body fluid or body tissue containing inflammation-specific monocytes comprises extracting patient-specific induced pluripotent stem cells, such as for example blood cells or skin cells, from the patient and performing a reprogramming factors-mediated de-differentiation of stem cells from the patient and extracting the inflammation-specific monocytes from the patient-specific induced pluripotent stem cells of the patient, as will be understood by those with skill in the art with respect to this disclosure. Any other suitable method can also be used for obtaining a body fluid or body tissue containing inflammation-specific monocytes, as will be understood by those with skill in the art with respect to this disclosure.

In one embodiment, the method further comprises purifying the inflammation-specific monocytes (ISMs). In one embodiment, purifying the inflammation-specific monocytes comprises performing fluorescence-activated cell sorting. In another embodiment, purifying the inflammation-specific monocytes comprises performing magnetic-activated cell sorting.

In one embodiment, the method further comprises expanding and storing at least some of the isolated inflammation-specific monocytes for multiple repeated infusions, as will be understood by those with skill in the art with respect to this disclosure. In one embodiment, expanding and storing at least some of the isolated inflammation-specific monocytes comprises freezing the isolated inflammation-specific monocytes.

Then, the method comprises producing gene-modified, inflammation-specific monocytes from the inflammation-specific monocytes, where the gene-modified, inflammation-specific monocytes comprise a 1-alpha-hydroxylase gene, where the 1-alpha-hydroxylase gene is expressed to produce functional 1-alpha-hydroxylase enzyme when the monocytes transdifferentiate into gene-modified, inflammation-specific macrophages. In one embodiment, the 1-alpha-hydroxylase gene is a human 1-alpha-hydroxylase gene. In one embodiment, the 1-alpha-hydroxylase gene is on plasmid DNA. In another embodiment, the 1-alpha-hydroxylase gene is on a viral vector. In a preferred embodiment, producing the gene-modified, inflammation-specific monocytes comprises transducing the purified inflammation-specific monocytes with the 1-alpha-hydroxylase gene. In one embodiment, transducing the purified inflammation-specific monocytes is accomplished by electroporation with one or more than one plasmid DNA or one or more than one viral vector comprising the 1-alpha-hydroxylase gene.

In one embodiment, the gene-modified, inflammation-specific monocytes further comprise one or more than one growth factor gene, where the one or more than one growth factor gene is expressed to produce a functional growth factor when the monocytes transdifferentiate into gene-modified, inflammation-specific macrophages, and where the growth factor enhances the function of calcitriol (the product of the 1-alpha-hydroxylase gene). In one embodiment, the growth factor gene is a human growth factor gene. In one embodiment, the growth factor gene is on plasmid DNA. In another embodiment, the growth factor gene is on a viral vector. In one embodiment, the growth factor gene is selected from the group consisting of insulin-like growth factor 1 (IGF-1) (also known as somatomedin C) and transforming growth factor beta gene (TGF-β), though other growth factor genes can be used, as will be understood by those with skill in the art with respect to this disclosure. In a preferred embodiment, producing the gene-modified, inflammation-specific monocytes comprising the one or more than one growth factor gene comprises transducing the purified inflammation-specific monocytes with one or more than one growth factor gene. In one embodiment, transducing the purified inflammation-specific monocytes with one or more than one growth factor gene is done simultaneously with transducing the purified inflammation-specific monocytes with the 1-alpha-hydroxylase gene. In another embodiment, transducing the purified inflammation-specific monocytes with one or more than one growth factor gene is done serially with transducing the purified inflammation-specific monocytes with the 1-alpha-hydroxylase gene. In another embodiment, transducing the purified inflammation-specific monocytes with one or more than one growth factor gene comprises using the one or more than one plasmid DNA or one or more than one viral vector comprising the one or more than one growth factor gene. In a preferred embodiment, transducing the purified inflammation-specific monocytes with one or more than one growth factor gene is done by electroporation with the one or more than one plasmid DNA or the one or more than one viral vector, where the one or more than one plasmid DNA or the one or more than one viral vector comprises the one or more than one growth factor gene. In a preferred embodiment, the plasmid DNA comprises both the 1-alpha-hydroxylase gene and the one or more than one growth factor gene. In another preferred embodiment, the viral vector comprises both the 1-alpha-hydroxylase gene and the one or more than one growth factor gene.

In one embodiment, the gene-modified, inflammation-specific monocytes further comprise one or more than one macrophage-specific promoter, where the one or more than one macrophage-specific promoter tends to limit the expression of the 1-alpha-hydroxylase gene, and when present, the one or more than one growth factor gene, to macrophages that transdifferentiate from the gene-modified, inflammation-specific monocytes. In one embodiment, the one or more than one macrophage-specific promoter is a human macrophage-specific promoter. In one embodiment, the one or more than one macrophage-specific promoter is on plasmid DNA. In another embodiment, the one or more than one macrophage-specific promoter is on a viral vector. In one embodiment, one or more than one of the one or more than one macrophage-specific promoter is selected from the group consisting of CD11b (Mac-1), CD14, c-fms, Lysozyme M and Scavenger Receptor Class A (SRA). Other macrophage-specific promoters can also be used, as will be understood by those with skill in the art with respect to this disclosure. In a preferred embodiment, producing the gene-modified, inflammation-specific monocytes comprising the 1-alpha-hydroxylase gene and the one or more than one macrophage-specific promoter comprises transducing the purified inflammation-specific monocytes with the 1-alpha-hydroxylase gene and the one or more than one macrophage-specific promoter. In one embodiment, transducing the purified inflammation-specific monocytes with the 1-alpha-hydroxylase gene and the one or more than one macrophage-specific promoter comprises using one or more than one plasmid DNA comprising both the 1-alpha-hydroxylase gene and the one or more than one macrophage-specific promoter. In another embodiment, transducing the purified inflammation-specific monocytes with the 1-alpha-hydroxylase gene and the one or more than one macrophage-specific promoter comprises using one or more than one viral vector comprising both the 1-alpha-hydroxylase gene and the one or more than one macrophage-specific promoter.

Next, the method comprises administering an amount of the gene-modified, inflammation-specific monocytes to the patient. In one embodiment, administration comprises a route selected from the group consisting of intraperitoneal administration, intramuscular administration, and intravenous infusion. In another embodiment, administration comprises infusion of the gene-modified, inflammation-specific monocytes into or adjacent to the inflamed tissue or organ. In one embodiment, the amount is between one hundred thousand and one billion cells. In another embodiment, the amount is between one million and one billion cells. In another embodiment, the amount is between one million and one hundred million cells. In another embodiment, the amount is between one million and ten million cells.

Then, the method comprises allowing the gene-modified, inflammation-specific monocytes to locate and enter into the inflamed organ or tissue affected by the condition or disease. Next, the method comprises allowing the gene-modified, inflammation-specific monocytes to transdifferentiate into gene-modified, inflammation-specific macrophages.

Then, the method comprises allowing activation of the one or more than one macrophage-specific promoter, thereby causing the gene-modified, inflammation-specific macrophages to produce 1-alpha-hydroxylase, where production of the 1-alpha-hydroxylase causes the localized production of calcitriol in the inflamed organ or tissue from circulating calcidiol which is present in body fluids of the patient, thereby treating the inflammation-related condition or disease by suppressing inflammation while limiting side effects, especially systemic hypercalcemia. In one embodiment, the gene-modified, inflammation-specific macrophages comprise one or more than one growth factor gene, and the method further comprises allowing the gene-modified, inflammation-specific macrophages to produce one or more than one growth factor from the one or more than one growth factor gene. Production of the one or more than one growth factor acts synergistically with the localized production of calcitriol to suppress inflammation, thereby further treating the inflammation-related condition or disease. The activation of the macrophage-specific promoter to turn on the 1-alpha-hydroxylase gene, and the growth factor gene if present, occurs automatically in the affected tissue without additional intervention. Once the treatment is complete, the gene-modified, inflammation-specific macrophages undergo apoptosis leading to termination of gene expression and preventing long term side effects of the treatment.

Example I: Demonstration of Efficacy of Agents to Produce Calcitriol In Vivo from Exogenous Calcidiol The efficacy of disclosed agents to produce calcitriol in vivo was demonstrated as follows. First, bicistronic lentiviral construct which was used to express human 1-alpha-hydroxylase gene (CYP) under the control of the macrophage-specific Mac1 promoter was prepared. GFP or mCherry expressed under the control of the universal PGK promoter was added to the construct to aid simultaneous monitoring of effective transduction efficiency. Then, 293T cells were transiently transfected with either Mac1-GFP-PGK-mCherry (negative control) or Mac1-CYP-PGK-GFP plasmid DNA. At 24 hours post-transfection, the 293T cells were incubated with 2.5 µM calcidiol to provide substrate for the 1-alpha-hydroxylase enzyme. After 12 hours incubation, conditioned medium was collected and calcitriol levels were measured by radioimmunoassay (MA) after removal of binding proteins. In the presence of the substrate calcidiol, 293T cells transfected with the Mac1-CYP-PGK-GFP plasmid synthesized calcitriol at a concentration of about 16,000 pg/mL, while production of calcitriol was negligible in the absence of the substrate demonstrating that such agents exhibited a very high capacity to synthesize calcitriol from exogenous calcidiol.

Example II: Demonstration of Efficacy of Agents and Methods

The efficacy of the disclosed agents and the method was demonstrated as follows. First, a bone marrow transplantation approach was used to generate Gr1+ monocytes comprising a Mac1-CYP (Mac1-1-alpha-hydroxylase gene) transgene for adoptive transfer. Eight-week-old C57BL/5 (B6) female mice were subjected to gamma-irradiation (10 Gy) to ablate endogenous hematopoietic cells. Next, one million Sca1-positive hematopoietic stem cells (HSCs) were transduced with either Mac1-GFP or Mac1-CYP lentiviral vector. Then, one million of the Sca1-positive hematopoietic stem cells transduced with Mac1-GFP (the controls) or Mac1-CYP lentiviral vector were transplanted to each of the irradiated mice through injection via tail. Over 70% of monocytes isolated from the bone marrow transplants was derived from the donor Sca1+HSCs.

Four weeks after marrow transplantation, Gr1-positive monocytes were isolated from bone marrow transplants taken from the mice. Another groups of B6 recipient mice were divided into four groups, where one group was untreated (the control group), and three groups had inflammatory bowel disease induced by oral administration of dextran sodium sulfate (3% DSS in drinking water) for six days. Of the induced groups, one group was untreated, one group was treated with one million of the isolated Gr1-positive monocytes comprising Mac1-GFP transgene, the other group was treated with one million of the isolated Gr1-positive monocytes comprising Mac1-CYP transgene. The mice were sacrificed at twelve days after induction of inflammatory bowel disease.

The one-time infusion of monocytes comprising Mac1-CYP transgene nearly completely ameliorated inflammatory bowel disease as evidenced by the following: 1) mice treated with the monocytes comprising Mac1-CYP transgene not only prevented further body weight loss but essentially regained the body weight lost during the disease induction phase ending with a body weight about 95% of that of the non-induced mice; 2) all mice treated with the monocytes comprising Mac1-CYP transgene survived while 30% of untreated mice died during the test period; and 3) mice treated with the monocytes comprising Mac1-CYP transgene had increased colon length and robust regeneration of the lost colonic crypts similar to non-induced mice. Additionally, mice treated with the monocytes comprising Mac1-CYP transgene did not show a significant increase in serum calcium levels confirming the macrophage specificity of the promoter Mac1. By comparison, mice treated with the monocytes comprising Mac1-GFP moderately reduced further body weight loss during the recovery phase but did not regain the body weight already lost, and had about the same mortality rate, colonic length and mucosal damage as untreated mice.

Therefore, the disclosed agents and method demonstrated the high efficiency of the present invention to treat inflammatory bowel disease without the side effect of systemic hypercalcemia.

Example III: Demonstration of Efficacy of Agents and Methods

The efficacy of the disclosed agents and the method was demonstrated as follows. First, Gr1+ monocytes were isolated from bone marrow cells of C57BL/6 mice and treated with M-CSF (100 ng/mL) for seven days to induce formation of premature M2 macrophages. These M2 monocytes stained positively for both CD11b and Gr1. These M2 macrophages were effectively transduced by the lentiviral vector in that approximately 70% of these transduced cells expressed the GFP transgene. The M2 macrophages were isolated and then were transduced with the lentiviral vector expressing either the human 1-alpha-hydroxylase gene driven by the Mac1 promoter (Mac1-CYP) or the green fluorescent protein gene driven by the Mac1 promoter (Mac1-GFP) (the control). Inflammatory bowel disease was induced in B6 mice by oral administration of dextran sodium sulfate for six days (3% DSS in drinking water). The one million of the genetically modified M2 macrophages were then injected per mouse via tail vein to each inflammatory bowel disease induced mouse at day seven. The mice were sacrificed seven days after infusion of the genetically modified M2 macrophages.

As seen with Mac1-CYP Gr1+ monocytes, Example II above, inflammatory bowel disease induced mice treated with a single infusion of Mac1-CYP M2 macrophages showed substantial repair of the severely damaged mucosa, the prevention of body weight loss and increased colon length. Further as seen with Mac1-CYP Gr1+ monocytes, Example II above, inflammatory bowel disease induced mice treated with a single infusion of Mac1-CYP M2 macrophages did not develop systemic hypercalcemia.

Therefore, the agents and method according to the present invention demonstrated the high efficiency of the present invention to treat inflammatory bowel disease without the side effect of systemic hypercalcemia.

Example IV: Demonstration of Efficacy of Agents and Methods

The efficacy of the disclosed agents and the method was demonstrated as follows. Sca1-positive hematopoietic stem cells (HSCs) were transduced with either Mac1-CYP-PGK-GFP (Mac1-1-alpha-hydroxylase-phosphoglycerate kinase-green fluorescent protein gene) lentiviral vector or with SFFV-CYP (spleen focus-forming virus-alpha-hydroxylase gene) lentiviral vector. Eight-week old B6 recipient mice were subjected to whole body lethal gamma ray irradiation (10 Gy). Immediately after irradiation, one million of the Sca1-positive transduced hematopoietic stem cells were transplanted to each of the irradiated mice through injection via tail. Engraftment was confirmed by determining the percentage of GFP+ cells in the circulation. After full engraftment, Experimental Autoimmune Encephalomyelitis (EAE) was induced by subcutaneous injection of the myelin specific antigens (MOG) 35-55 peptide, which initiated the peripheral activation of myelin specific CD4+ T cells, which then migrated to the central nervous system and induced an immune reaction. Clinical scores that describe the relative severity of Experimental Autoimmune Encephalomyelitis were monitored on a daily basis for four weeks. Recipient mice transplanted with hematopoietic stem cells that were transduced with the Mac1-CYP-PGK-GFP lentiviral vector exhibited delayed onset of symptoms (sixteen days compared with six days) and a reduction in peak disease activity (clinical score of between 1.0 and 1.5, compared with a clinical score of between 3.0 and 3.5). Therefore, the disclosed agents and method demonstrated the high efficiency of the present invention to treat inflammatory brain disease without the side effect of systemic hypercalcemia.

Example V: Demonstration of Efficacy of Agents and Methods

The efficacy of the disclosed agents and the method was demonstrated as follows. First, specific targeting of inflamed tissues by CD11b+/Gr1+ monocytes in mice, which correspond to human CD14+CD16-monocytes, was demonstrated. Inflammatory bowel disease (IBD) was induced in 8-week-old C57BL/6 (B6) female mice by oral administration of dextran sodium sulfate (DSS) (3% in drinking water for 7 days and 1% thereafter), which is a generally accepted mouse model for human inflammatory bowel disease. At day 5, 0.1 mL of clodronate-lyposome complex was injected intravenously to reduce endogenous monocytes. At day 7, the inflammatory bowel disease mice or healthy control mice were injected intravenously with CD11b+/Gr1+ monocytes (2 million cells/mouse) isolated from green fluorescent protein (GFP) transgenic mice. Green fluorescent protein produced in these monocytes allowed localization of the position of the infused monocytes. At day 10, the mice were perfused with phosphate-buffered saline (PBS) to remove un-engrafted exogenous monocytes. Tissues were collected for detection of the green fluorescent protein marker in collected tissues and it was found that injected Gr1+ monocytes migrated only to the inflamed colon of inflammatory bowel disease mice but not to the colon of healthy mice.

Second, the disclosed agents and method were used to treat dextran sodium sulfate-induced inflammatory bowel disease in mice as a model for human inflammatory bowel disease to test the efficacy of the agents and method according to the present invention. CD11b+/Gr1+ monocytes were isolated from the bone marrow or blood of the mice using magnetic-activated cell sorting (CD11b+/Gr1+ monocytes correspond to human CD14+CD16-monocytes). The isolated monocytes were electroporated with either CD14-mCherry-PGK-GFP plasmid DNA or CD14-CYP27b1-PGK-GFP plasmid DNA. The electroporated monocytes were injected systemically in the inflammatory bowel disease mice. Migration of injected monocytes to inflamed colon was demonstrated by green fluorescent protein staining of colon sections upon histological examination. Severe mucosal damage and inflammatory cell infiltration occurred in the colon of the dextran sodium sulfate-treated mice. These pathologic damages were significantly reduced by intravenous injection of monocytes expressing the 1-alpha-hydroxylase gene, but not reduced by injection of monocytes expressing only a non-therapeutic marker gene.

Then, the efficacy of the disclosed agents and method was confirmed in an additional study. Six groups of animals were used in this study: Group 1: control healthy mice; Group 2: mice that were treated with dextran sodium sulfate to induce inflammatory bowel disease but that did not receive any therapy; Group 3: mice that were treated with dextran sodium sulfate to induce inflammatory bowel disease and that received intraperitoneal injections with calcitriol (200 ng/day/mouse) (the positive control group); Group 4: mice that were treated with dextran sodium sulfate to induce inflammatory bowel disease and that received intravenous injections with monocytes electroporated with CD14 promoter-mCherry plasmid (the negative control group); Group 5: mice that were treated with dextran sodium sulfate to induce inflammatory bowel disease and that received intravenous injections with monocytes electroporated with CD14 promoter-1-alpha-hydroxylase gene plasmid (the treatment group); Group 6: mice that were treated with dextran sodium sulfate to induce inflammatory bowel disease and that received intravenous injections with monocytes electroporated with plasmids expressing both 1-alpha-hydroxylase gene and transforming growth factor beta gene (a second treatment group). Injections were made at day 7 post-disease induction by dextran sodium sulfate. All mice were sacrificed at day 10.

At day 7 post-dextran sodium sulfate treatment, mice lost 20-25% of their body weight. In the absence of any therapeutic treatment (Group 2), these inflammatory bowel disease mice lost an additional 15-18% of their body weight by Day 8-10. About 50% of mice receiving no treatment had to be sacrificed in order to obtain blood and live tissue samples, as they were too weak to survive by Day 10. Systemic calcitriol injections failed to prevent body weight loss. While injection of monocytes expressing non-therapeutic genes (mCherry) reduced body weight loss, injection of monocytes expressing 1-alpha-hydroxylase gene alone or together with transforming growth factor beta gene was more effective in reducing weight loss. In contrast to a more than 30% increase in serum calcium in the calcitriol-treated inflammatory bowel disease mice, no hypercalcemia occurred in inflammatory bowel disease mice receiving injection of monocytes expressing 1-alpha-hydroxylase gene alone or in combination with transforming growth factor beta gene. Thus, the method for treating one or more than one inflammation-related condition or disease according to the present invention prevented body weight loss in dextran sodium sulfate mice but did not cause hypercalcemia. Injection of monocytes overexpressing non-therapeutic mCherry marker gene did not markedly reduce the severity of colon lesions. In contrast, injection of monocytes overexpressing the 1-alpha-hydroxylase gene not only prevented body weight loss but also dramatically reduced the lesion area. Systemic calcitriol injections failed to prevent body weight loss, however, it did improve colon mucosal integrity. This discrepancy is probably due to the suppression of inflammation by the high dose of calcitriol, while the severe hypercalcemia it caused led to a deterioration of the overall health of the mice. Therefore, the disclosed inflammation-specific monocytes-based 1-alpha-hydroxylase gene adoptive therapy is highly effective in treating inflammatory bowel disease without producing a general systemic hypercalcemia.

The method for treating one or more than one inflammation-related condition or disease has several advantages compared with other cell-based gene therapies. First, the present method does not require prolonged ex-vivo cell culture and expansion, thereby substantially reducing the cost of the treatment. Second, based on the animal studies above, a single injection of gene-modified, inflammation-specific monocytes was sufficient to treat the disease, though the present invention includes the use of multiple doses if needed. Third, the only product of the 1-alpha-hydroxylase gene in humans is calcitriol, which is harmless to the body as long as the overexpression of calcitriol is limited to the diseased tissue preventing systemic hypercalcemia. Fourth, transduction of the monocytes with the 1-alpha-hydroxylase gene can be made by electroporation of naked plasmic DNA which does not involve the use of any viral vector for gene transfer, thereby eliminating any risk associated with the use of viral vectors, though the present method includes the use of viral vectors when warranted.

Dendritic Cells (DCs) Engineered for Constitutive Expression of Two Enzymes: 1 α Hydroxylase and Retinaldehyde Dehydrogenase 2

Inflammatory diseases in the intestines, including but not limited to, inflammatory bowel diseases (IBDs) can be treated by utilizing the methods and treatments described herein. IBDs are a group of diseases that are associated with conditions of chronic inflammation in the gastrointestinal tract. These diseases display high morbidity and do not have a cure. Therefore, IBD patients have unmet therapeutic needs.

Because recent data suggest that IBD is due to abnormal responses of our immune system to commensal bacteria, new medications have been developed to inhibit functions of the molecules that mediate the pathogenic immune responses. Examples of these new medications are TNFα and α4β7 blockers. However, the molecules targeted by those medications are equally important for immune defense, e.g. immunity against infections. It is therefore possible that functional blocking of these molecules could pose threats to patients' health. In this regard, some of the side effects, e.g. increased chances of infections and cancers, observed in patients who received these novel therapies, are presumably due to a compromised systemic immunity. It is therefore desirable to regulate IBD without these side effects.

A significant challenge in treating IBD and related inflammatory disorders is targeted suppression of inflammation in the inflamed intestines but without compromising a patient's general immunity to flight other diseases. In this regard, down regulation of one's own immunity against infections and cancers as a result of unattended suppression of the actions of one or more inflammation-related molecules in response to the treatment could be detrimental and may even be lethal. For this reason, scientists have been diligently looking into mechanisms that cause specific inflammation in the intestines. IBD patients experience specific attacks of intestines by their own immune system. These specific attacks are caused by a subset of immune cells that can specifically recognize the intestines (i.e. intestine-specific pathogenic immune cells). These intestine-specific pathogenic immune cells are also present in normal healthy control individuals but controlled by regulatory mechanisms in the immune system. These regulatory mechanisms are now known to be mediated mostly by another subset of immune cells, i.e. regulatory T (Treg) cells. Therefore, Treg cells are highly specific as shown by the fact that Treg cells responsible for controlling other pathogenic immune cells (e.g. those that can cause type 1 diabetes) are intact in IBD patients. Therefore, identification and functional reinvigoration of Treg cells that are responsible for specific control of intestine-specific pathogenic immune cells represent one of the major scientific endeavors in searching a cure for IBDs.

However, generation of Treg cells that can specifically regain control of intestine-specific pathogenic immune cells is challenging. Two strategies for generating Treg cells are being pursued. The first strategy is that Treg cells are produced and injected into animals. Although several methods have been well established for manufacturing Treg cells in cell culture, an agonizing issue is the instability of the injected Treg cells in animals. The second strategy is that Tregs cells are directly induced in animals. Unfortunately, current available techniques for inducing Treg cells in animals are not stable either.

Dendritic cells (DCs) engineered for constitutive expression of two enzymes can be utilized to suppress inflammation in the intestines, e.g. inflammatory bowel diseases (IBDs). The dendritic cells have the capacity to home to peripheral lymphoid tissues. The first enzyme can be 1α hydroxylase that is the physiological enzyme for producing the active vitamin D metabolite [i.e. 1,25(OH)2D]. The second enzyme can be retinaldehyde dehydrogenase 2 (RALDH2) that is the physiological enzyme for producing one of the active vitamin A metabolites (i.e. retinoid acid or RA). The engineered DCs can induce regulatory T (Treg) cells, a subset of immune cells, which have specific gut-honing capacity (i.e. gut-homing Treg). Since Treg cells are known to suppress inflammation, the engineered DCs can specifically suppress inflammation in the intestines, e.g. inflammatory bowel diseases (IBDs). The DCs have the capacity to home to peripheral lymphoid tissues. Therefore, engineered DCs can be used to bring the 1a-hydroyxlase and the RALDH2 to the peripheral lymphoid tissues where the 1a-hydroxylase produces calcitriol and the RALDH2 produces retinoic acid (RA). Consequently, the combined action of calcitriol and RA can induce in the peripheral lymphoid tissues the gut-homing Treg cells that can subsequently specifically migrate into and reinstate immune tolerance in the gut.

A method to directly induce in mammals stable Treg cells that can uniquely regain control of intestine-specific pathogenic immune cells is described herein. In this respect, this technology will allow direct induction of Treg cells that have specific gut-homing capacity (i.e. gut-homing Treg) in the peripheral immune organs of a mammal. Because of specific gut-homing ability, the gut-homing Treg cells induced can then specifically migrate into the inflamed intestines to arrest inflammation. Specifically, autologous dendritic cells (DCs), a subset of immune cells, for expression of both 1α hydroxylase and retinaldehyde dehydrogenase 2 (RALDH2) can be engineered. The 1α hydroxylase is the physiological enzyme for converting 25(OH)D into 1,25(OH)2D (the active vitamin D metabolite). The retinaldehyde dehydrogenase 2 (RALDH2) is the enzyme mediating production of retinoid acid (RA) (one of the active vitamin A metabolites) in vivo. Because DCs are endowed with the capacity to specifically migrate into peripheral lymphoid organs, the engineered DCs, after administered into a mammal through intravenous or subcutaneous injection, can create focally high concentrations of 1,25(OH)2D and RA in the peripheral lymphoid organs. Because 1,25(OH)2D is able to program Treg cells and RA can induce expression of gut-homing receptors on T cells, the injected DCs can induce Tregs cells that express gut-homing receptors (i.e. gut-homing Treg) in the peripheral lymphoid organs. The gut-homing Treg cells can specifically home to and act to suppress inflammation in the gut.

Inflammatory monocytes engineered for constitutive expression of 1α hydroxylase to treat inflammation-related diseases has been described herein. The use of 1α hydroxylase is common between the inflammatory monocytes and the engineered DCs. However, the technology for the use of 1α hydroxylase in DCs differs from the use of 1 α hydroxylase with inflammatory monocytes in three major aspects: 1) the use of 1α hydroxylase in DCs involves genetically-modified DC cells that can specifically migrate into peripheral lymphoid organs to promote generation of inflammation suppressing Treg cells rather than using genetically modified macrophages as the targeting vehicles; 2) the 1α hydroxylase in DC is to program naive T cells into gut-homing Treg cells to fight inflammation rather than to produce a high concentration of 1,25(OH)2D for suppressing inflammation locally per se; and 3) the use of 1α hydroxylase in DCs also involves increased expression of RALDH2 (to produce RA) to enhance gut homing ability of Treg cells.

Dendritic cells (DC) are the most important antigen presenting cells and show promise in cell-based immunotherapy. In some embodiments, the cell-based immunotherapy can include the acquisition of gut-homing capacity in antigen-specific T cells through DC vaccination for the treatment of gut-related diseases. However, data has shown that ex vivo-generated DCs lose their ability to induce expression of gut-homing receptors on T cells. Since retinoic acid has been shown to imprint T cells with gut tropism, this strategy may be implemented to restore the DCs' capacity to induce expression of the gut homing receptors (i.e. the α4β7 and CCR9) in antigen-specific T cells.

DCs were generated by culturing bone marrow mononuclear cells in the presence of GM-CSF and IL-4. Using a lentiviral vector, the monocyte-derived DCs were engineered to constitutively express retinaldehyde dehydrogenase 2 (RALDH2), the enzyme that is responsible for converting retinal into retinoic acid. The expression of the ALDHIA2 gene which encodes the RALDH2 was confirmed by real time quantitative polychain reaction. The intracellular expression of the RALDH2 as well as its enzymatic function was further verified by the flow cytometry.

To evaluate the capacity of the engineered DCs to induce the gut-homing receptors in antigen-specific T cells, mice were subcutaneously injected with a peptide (OTII)-pulsed DCs that were engineered for over expression of the RALDH2 (RALDH2-DC) or untreated (Control-DC). Ten days later, local draining lymph nodes were examined for expression of the CCR9 and α4β7 on the peptide-specific T cells by the multichromatic flow cytometry. The data showed that CCR9 expression on the T lymphocytes in the draining lymph nodes of the mice injected with the OTII-pulsed RALDH2-DC but not Control-DC was significantly increased. The data therefore suggest that DCs engineered for over expression of the RALDH2 can be used for developing antigen-specific immunotherapies for gut-related diseases.

A major challenge of IBD therapy is targeted suppression of unwanted inflammation in the inflamed intestines without compromising the patient's general immunity. For example, any down regulation of immunity against infections and cancers due to blocking of an inflammation-related molecule in response to current therapies could be detrimental and even lethal. IBD patients experience specific attacks of intestines by their own immune system. These specific attacks are caused by a subset of immune cells that can specifically recognize the intestines (hereafter "intestine-specific pathogenic immune cells"). These intestine-specific pathogenic immune cells are also present in normal healthy control individuals but controlled by regulatory mechanisms in the immune system. These regulatory mechanisms are mediated primarily by another subset of immune cells, i.e. regulatory T (Treg) cells. Identification and functional reinvigoration of Treg cells that are responsible for specific control of intestine-specific pathogenic immune cells represent one of the major scientific endeavors in searching a cure for IBDs.

However, generation of Treg cells that can specifically regain control of intestine-specific pathogenic immune cells can be challenging. Two strategies for generating Treg cells can be pursued. The first strategy is that Treg cells are generated in cell cultures and infused back in vivo. Although several methods have been well established for in vitro production of Treg cells, an issue is the instability of in vivo generated Treg cells that, after being infused back in vivo, may potentially revert into pathogenic immune cells. In some embodiments, the second strategy is that Tregs cells are directly induced in vivo. Tolerogenic dendritic cells (DCs) can be pursued for this purpose. However, because tolerogenic DCs themselves are generated in cell cultures, instability of tolerogenic DCs can also be a matter of concern.

A method for programming naïve T cells in the peripheral lymphoid organs into Treg cells that can uniquely regain control of intestine-specific pathogenic immune cells (i.e. the immune cells that cause inflammation in the intestines) in vivo is developed as shown in FIG. 1. In this respect, the agents and methods described can allow direct in vivo induction in the peripheral immune organs of stable Treg cells that have specific gut-homing capacity (i.e. gut-homing Treg). Because of the specific gut-homing ability, the gut-homing Treg cells can specifically migrate into intestines to suppress inflammation locally in the inflamed guts without affecting other healthy organs. Specifically, DCs for constitutive expression of two enzymes can be engineered.

The first enzyme is 1α hydroxylase that is the physiological enzyme for converting 25(OH)D, i.e. the inactive vitamin D metabolite in the serum, into 1,25(OH)2D, i.e. the active vitamin D metabolite. Therefore, DCs that constitutively express 1α hydroxylase (hereafter DC-CYP27B1 in which CYP27B1 is the gene that encodes 1α hydroxylase), following in vivo injection, will migrate into and actively produce 1,25(OH)2D in the peripheral immune organs [e.g. lymph nodes that drain the injection sites (hereafter dLNs)] as shown in FIG. 1. Since a major function of DCs is to program naive T cells and 1,25(OH)2D has been shown to program naïve T cells into Treg cells, the DC-CYP27B1 cells are able to induce Treg cells in the peripheral lymphoid organs. The data as described herein demonstrates that in vivo injection of DC-CYP27B1 cells results in induction of Treg cells independent of DC status. Therefore, this treatment or method does not have the instability concern.

The second enzyme is retinaldehyde dehydrogenase 2 (RALDH2) that is the physiological enzyme for producing retinoid acid (RA), one of the active vitamin A metabolites. Therefore, DCs that constitutively express RALDH2 (hereafter DC-ALDH1a2 in which ALDH1a2 is the gene that encodes RALDH2), following in vivo injection, will migrate into and actively produce RA in the peripheral lymphoid organs. RA can imprint gut-homing receptors on T cells (hereafter gut-homing T cells), the DC-ALDH1a2 cells are able to induce gut-homing T cells in the peripheral lymphoid organs. The data as described herein shows that in vivo injection of DC-ALDH1a2 cells results in induction of gut-homing T cells.

DCs engineered for constitutive expression of both 1α hydroxylase and RALDH2 (hereafter DC-CYP27B1-ALDH1a2), following in vivo injection, can migrate into and actively produce 1,25(OH)2D and RA in the peripheral lymphoid organs. The high concentrations of 1,25(OH)2D and RA at the DC-T cell interface in the peripheral lymphoid organs are expected to program naive T cells into Treg cells that express gut-homing receptors (i.e. gut-homing Treg). These gut-homing Treg cells are able to specifically migrate into and arrest inflammation in the intestines as shown in FIG. 1.

Current therapeutic applications of 1,25(OH)2D in humans have mostly failed despite strong preclinical evidence for its immunomodulatory function. The failure could be due to inability of current clinical modalities to increase 1,25(OH)2D concentration to a therapeutic level in the blood which is inevitably accompanied by a serious side effect, i.e. hypercalcemia. Hypercalcemia means an abnormally high calcium level in the blood as a result of a high blood 1,25(OH)2D concentration. The reason for the attending hypercalcemia is that a concentration significantly higher than hypercalcemia threshold appears to be necessary for 1,25(OH)2D's immunomodulatory function. In contrast to current clinical modalities, DC-CYP27B1-ALDH1a2, following in vivo delivery, does not result in a high blood 1,25(OH)2D concentration; instead, it should mainly migrate into and create a focally high 1,25(OH)2D concentration in the peripheral lymphoid organs. Consequently, DC-CYP27B1-ALDH1a2 cells can induce Treg cells without the risk of hypercalcemia. This method does not cause high RA concentration in the blood and potential side effects can be avoided.

In some embodiments, inflammatory monocytes engineered for constitutive expression of 1α hydroxylase can be utilized for the treatment of inflammation-related diseases including but not limited to IBDs. It has been shown that the engineered inflammatory monocytes provides previously unreachable therapeutic effect of the active vitamin D metabolite on experimental colitis. In relation to DCs, evidence has been provided that DC-CYP27B1 cells provide much stronger suppression of experimental colitis. Therefore, an even greater suppression of experimental colitis using DC-CYP27B1-ALDH 1 a2 can be achieved. Therefore, the strategy described herein for treating with DCs can be suitable for treating inflammation in the intestines including but not limited to IBDs. Moreover, the method of using genetically modified macrophages, which have homing ability to inflammation sites, is described as a vehicle to increase local 1,25(OH)2D concentration to fight inflammation and autoimmune diseases without causing the adverse effect of hypercalcemia. The genetically-modified DC cells differ from the genetically modified macrophages in three major aspects: 1) genetically-modified DC cells involves genetically-modified DC cells that can specifically migrate into peripheral lymphoid organs to promote generation of inflammation suppressing Treg cells rather than using genetically modified macrophages as the targeting vehicles; 2) the 1α hydroxylase in DC is to program naive T cells into gut-homing Treg cells to fight inflammation rather than to produce a high concentration of 1,25(OH)2D for suppressing inflammation locally per se; and 3) it also involves increased expression of RALDH2 (to produce RA) to enhance gut homing ability of Treg cells. Therefore, the agents and methods of utilizing genetically-modified DC cells lead to a highly focused suppression of gut inflammations, including but not limited to IBDs, without compromising a patient's general immunity and health.

The methods and agents disclosed herein can be used to mainly treat inflammatory bowel diseases (IBDs); however it may be applicable to the therapies of other inflammatory diseases in the intestines. The therapeutic effect can be achieved through induction of gut-homing regulatory T cells (i.e. gut-homing Treg) in the peripheral lymphoid organs such that the Treg cells can specifically migrate into and suppress inflammation in the inflamed intestines. The induction of gut-homing Treg cells can be accomplished through intravenous or subcutaneous injection of dendritic cells (DCs) engineered for constitutive expression of 1α hydroxylase and retinaldehyde dehydrogenase 2 (RALDH2). This DC type is also called DC-CYP27B1-ALDH1a2 in which CYP27B1 is the gene for producing 1α hydroxylase and ALDH1a2 is the gene for generating RALDH2. The DCs can be engineered for constitutive expression of 1α hydroxylase and retinaldehyde dehydrogenase 2 (RALDH2) through the use of a vector. The vector can include a vector backbone, a 1-alpha-hydroxylase gene that produces functional 1-alpha-hydroxylase and a retinaldehyde dehydrogenase 2 gene that produces functional retinaldehyde dehydrogenase 2. In some embodiments, a gene, including but not limited to TGF-beta and IL-10, may replace the 1-alpha-hydroxylase gene for induction of Treg cells. Bone-marrow- or PBMC (peripheral blood mononuclear cell)-derived dendritic cells can be transduced with the vector thereby generating the gene-modified, lymphoid-tissue-homing dendritic cell. The gene-modified, lymphoid-tissue-homing dendritic cell can be administered to a patient and after administration to the patient the gene-modified, lymphoid-tissue-homing dendritic cell can migrate into and actively produce 1,25(OH)2D and retinoid acid in peripheral lymphoid organs.

Inside the DC, 1α hydroxylase will produce the active vitamin D metabolite [i.e. 1,25(OH)2D] while RALDH2 will produce one of the active vitamin A metabolite (i.e. retinoid acid or RA). Because 1,25(OH)2D can induce Treg cells and RA is able to induce gut-homing receptors on T cells, DC-CYP27B1-ALDH1a2 following in vivo delivery will induce gut-homing Treg. Additionally, DC-CYP27B1-ALDH1a2 can create focally high concentrations of 1,25(OH)2D and RA in the peripheral lymphoid organs but not in the blood, thereby avoiding serious side effects that can be caused by high concentrations of these two metabolites in the blood [e.g. hypercalcemia that is caused by a high 1,25(OH)2D concentration in the blood and is hampering clinical applications of this active vitamin D metabolite].

In some embodiments, the method for generating dendritic cells (DCs) can stably express 1α hydroxylase (to program Treg cells) and RALDH2 (to induce gut-homing ability of Treg cells). This type of DC is referred to as DC-CYP27B1-ALDH1a2 in which CYP27B1 is the gene that encodes 1α hydroxylase and ALDH1a2 is the gene that expresses RALDH2. In some embodiments, the components in this method include: a) DCs; b) a vector that expresses both 1α hydroxylase and RALDH2. DCs generated from bone marrow or peripheral blood monocytes are transduced, following standard protocol, with the vector twice at days 4 and 6. On day 8, DCs are evaluated for expression of the two enzymes by flow cytometry.

In some embodiments, the method includes confirming enhanced expressions and functions of CYP27B1 and ALDH1a2 genes in DC-CYP27B1-ALDH1a2 cells. Main components in this method can include: a) DC-CYP27B1-ALDH1a2; b) CYP27B1- and ALDH1a2-specific primers for examining gene expressions of CYP27B1 and ALDH1a2 respectively using real time polychain reaction; c) fluorescence-conjugated anti-1α hydroxylase and anti-RALDH2 antibodies for examining protein expressions of 1α hydroxylase and RALDH2 respectively using flow cytometry; d) commercial kits for evaluating functions of 1α hydroxylase and RALDH2.

In some embodiments, the method includes evaluating whether intravenous and/or subcutaneous injection of DC-CYP27B1-ALDH1a2, as compared to DC-CYP27B1 and DC-ALDH1a2, provides a much stronger suppression of experimental colitis. Main components in this method can include: a) DC-CYP27B1-ALDH1a2; b) DC-CYP27B1; c) DC-ALDH1a2; d) fluorescence-conjugated anti-1a hydroxylase and anti-RALDH2 antibodies for examining protein expressions of 1α hydroxylase and RALDH2 respectively using flow cytometry. DCs are transduced by the relevant vectors and examined for expressions of relevant enzymes inside the DCs. More than 90% expressions of the relevant enzymes are required before the DCs are injected intravenously or subcutaneously into animals. Thus, animals are induced for colitis on day 0, treated with the engineered DCs on day 3, and monitored for colitis daily. Some animals are sacrificed for further examinations of intestine pathology and alterations in other important organs.

In some embodiments, the method involves evaluating whether intravenous and/or subcutaneous injection of DC-CYP27B1-ALDH1a2 induces gut-homing Treg cells in the peripheral lymphoid organs. Main components in this method can include: a) DC-CYP27B1-ALDH1a2; b) DC-CYP27B1; c) DC-ALDH1a2; d) fluorescence-conjugated antibodies for examining Treg cells in the peripheral lymphoid organs using flow cytometry. Animals are treated with the engineered DCs and monitored for induction of Treg cells in the peripheral lymphoid organs using flow cytometry.

In some embodiments, the method includes evaluating whether gut-homing Treg cells induced by intravenous and/or subcutaneous injection of DC-CYP27B1-ALDH1a2 can specifically migrate into inflamed intestines in animals with experimental colitis. Main components in this method can include: a) DC-CYP27B1-ALDH1a2; b) DC-CYP27B1; c) DC-ALDH1a2; d) fluorescence-conjugated reagents for examining Treg cells in the inflamed intestines and other tissues. To facilitate tracking of antigen-specific gut-homing Treg cells, the DCs are pulsed with a chicken ova peptide, i.e. Ova323-339 before being injected into animals. Animals are induced for colitis on day 0, treated with the engineered DCs on day 3, and sacrificed at various times for examining Treg cells in the inflamed intestines and other tissues using flow cytometry. The Ova323-339-specific Treg cells will be identified by Ova323-339 tetramers that are available from NIH tetramer core facility.

In some embodiments, the method for generating DC-CYP27B1-ALDH1a2 cells are suitable for human application. This human applicable DC-CYP27B1-ALDH1a2 is referred to as hDC-CYP27B1-ALDH1a2 in which "h" means human. Main components in this method can include: a) peripheral blood mononuclear cells (PBMCs); b) vector that expresses both enzymes and is suitable for human application; c) CYP27B1- and ALDH1a2-specific primers for examining gene expressions of CYP27B1 and ALDH1a2 respectively using real time polychain reaction; d) fluorescence-conjugated antibodies for evaluating expressions of 1α hydrolyxase and RALDH2 proteins; e) commercial kits for evaluating functions of 1α hydroxylase and RALDH2. DCs are generated from PBMCs, transduced with the vector, and evaluated for expressions and functions of the two enzymes.

In some embodiments, the method involves treating IBD patients using hDC-CYP27B1-ALDH1a2. Main components in this method can include: a) peripheral blood mononuclear cells (PBMCs); b) vector that expresses both enzymes and is suitable for human application; c) fluorescence-conjugated antibodies for evaluating expressions of 1α hydroxylase and RALDH2 proteins. DCs are generated from PBMCs, transduced with the vector, and evaluated for expressions of the two enzymes by flow cytometry. More than 90% expressions of the two enzymes are required before the DCs are injected intravenously or subcutaneously into patients. Patients under this treatment are monitored for vital signs for at least one week in the hospital and continuously followed up for IBD symptoms.

DC-CYP27B1 can induce Treg cells in the peripheral lymphoid organs and that DC-ALDH1a2 can induce gut-homing receptors on T cell surface. Data as described herein shows that DC-CYP27B1-ALDH1a2, as compared to DC-CYP27B1 and DC-ALDH1a2, provides a stronger suppression of experimental colitis. The vector can be optimized to expresses both 1α hydroxylase and RALDH2. In some embodiments, DC-CYP27B1-ALDH1a2, as compared to DC-CYP27B1 and DC-ALDH1a2, can provide a significantly enhanced suppression of colitis. The hDC-CYP27B1-ALDH1a2 can be produced that is ready to be commercialized for clinical trials.

EXAMPLES

The materials and methods described below can be used interchangeably with the examples disclosed herein.

Materials & Methods:

Mice

Female BALB/c mice can be purchased from The Jackson Laboratory (Bar Harbor, Me.). All mice were used at ages 5-8 weeks.

Induction of TNBS Colitis.

TNBS-colitis can be induced in 5-6 week-old female C57BL/6 mice according to previous reported method. Mortality and body weights can be recorded daily.

Cell Culture

DC2.4 cells are a murine bone marrow-derived DC line and can be obtained from Dr. Kenneth Rock (Dana Farber Cancer institute, Boston, Mass.). DC2.4 cells can be cultured in RPMI-1640 medium supplemented with 10% fetal bovine serum (FBS), 2 mM glutamine, 0.05 mM 2-mercaptoethanol and 100 µg/ml penicillin and streptomycin in 24-well plates in a humidified atmosphere containing 5% $CO_2$ at 37° C. Cells were passaged at 80-90% confluence.

Induction of FoxP3+ T Cells In Vitro

The naive mouse splenocytes can be cultured for 3 days with 1,25 Vitamin D (100 U/ml, Sigma-Aldrich) in the presence of human (h) IL-2 (50 U/ml) in complete RPMI 1640 medium (10% FBS; HyClone). The cells were harvested and stained for the FoxP3 expression with an anti-FoxP3 Ab (FJK-16s; eBioscience) and CCR9 expression.

Preparation of Plasmid Constructs.

The 1.6 kb mouse CYP27B1 cDNA and RALDH2 can be amplified by PCR using a plasmid containing the mouse CYP27B1 and RALDH2 cDNA plasmids. The amplified mCYP27B1 cDNA fragment with a 5' KOZAK ribosome entry sequence was cloned into the pRRL-SIN-.cPPt.PGKGFP.WPRE lentiviral vector (Addgene, Cambridge, Mass.). The resulting construct was designated SFFV-CYP-PGK-GFP. The amplified mRALDH2 cDNA fragment was cloned into the SFFV-CYP-PGK-GFP construct, and was named as SFFV-CYP-PGK-ALDH. This bicistronic plasmid expresses CYP27B1 controlled by the SFFV promoter and ALDH controlled by the nonspecific PGK promoter. In some embodiments, a lentiviral vector or other human applicable (e.g. AAV) vector can be used for administration to a human patient.

Lentiviral Vectors.

Lentiviral vectors can be produced in HEK-293T cells. HEK-293T cells can be transfected with the indicated transgene plasmid together with CMVVSVG and PAX2 plasmids using calcium phosphate method. Supernatants can be collected 48 hours after transient transfection and viral particles were concentrated by centrifugation for 24 hours at 6,000×g at 4° C. After removal of the supernatant, viral particles can be resuspended in phosphate-buffered saline (PBS) containing 5% glycerol and stored at −80° C. The biological titers were approximately $5 \times 10^7$ particles/mL as determined by FACS analysis of GFP+ cells in 293T cells transduced with various doses of the concentrated vectors.

In Vitro Evaluation of Cyp27b1 and Raldh2 Transgene Expression and Activity.

Primary DCs can be isolated from mouse bone marrow and transduced with either SFFV-CYP27B1 or SFFV-CYP27B1-PGK-ALDH lentiviral vector at a MOI of 3. After 2 days recovery, the cells can be seeded at a density of $0.5 \times 10^6$ cells/mL in 12-well plate and 25(OH)D3 was added to final concentration 2.5 μM. After 20 h incubation, cells can be harvested for total RNA isolation and the mRNA level of CPY27B1 can be measured by realtime PCR. 1,25(OH)2D3 concentration in the resulting conditioned medium can be determined by radioimmunoassay (MA). In some embodiments, the primary DCs can be bone-marrow or PBMC (peripheral blood mononuclear cell)-derived dendritic cells that can be transduced with the vector thereby generating the gene-modified, lymphoid-tissue-homing dendritic cell.

Flow Cytometry.

Transduced mCYP27B1-positive DC can be harvested, washed in PBS, resuspended in the FACS buffer and analyzed for GFP expression on a FACSAria II flow cytometer (BD Biosciences, San Jose, Calif.).The other staining procedures for FACS analysis were followed with the manufacturers' protocols.

Quantitative Real-Time RT-PCR.

Total RNA can be isolated from the cell and tissue samples using RNeasy mini kit (Qiagen, Valencia, Calif.). cDNA was prepared using the superscript III cDNA synthesis kit (Invitrogen), according to instructions. Real-time PCR was performed with SYBR Green PCR Master Mix (Applied Biosystems, Carlsbad, Calif.) in 7500 Fast Real Time PCR System (Applied Biosystems). The data were normalized to GAPDH as a reference and presented as fold change relative to control samples.

Immunohistological Analysis.

After flushing with cold PBS, a segment of the distal colon can be fixed in 4% paraformaldehyde. 10 μm-thick frozen sections can be stained with H&E (Sigma-Aldrich). Sections can be examined blindly and scored by a pathologist according to widely used Criteria.

Treg Suppression Assay.

Mouse CD4+T cells can be isolated from splenocytes of BALB/c from The Jackson Laboratory with the CD4 T cell isolation kit (Miltenyi Biotec). The CD4+ T cells can be incubated with CFSE according to manufacturer's protocols. CFSE+CD4 T cells were then co-cultured with lymphocytes isolated from MLN of previously immunized mice with DCs carrying different transgenes. In addition, T cell activators (immobilized anti-CD3 and anti-CD28 beads) can be added for 3 days in the co-culture before FACS analyses.

Statistical Analysis

Results are expressed as mean±SEM and statistically analyzed by Student's T test or One-Way ANOVA. A value of $P<0.05$ was considered statistically significant.

Example VI: Demonstration of Efficacy of Agents and Methods to Engineer Dendritic Cells to Constitutively Overexpress 1α-Hydroxylase and RALDH2

The efficacy of the disclosed agents and the methods for engineering dendritic cells to constitutively overexpress 1α-hydroxylase and RALDH2 was demonstrated as follows. In some embodiments, the primary DCs can be bone-marrow or PBMC (peripheral blood mononuclear cells)-derived dendritic cells that can be transduced with the vector thereby generating the gene-modified, lymphoid-tissue-homing dendritic cell. In some embodiments, a lentiviral vector or other human applicable (e.g. AAV) vector can be used for administration to a human patient. A lentiviral vector that carried both the CYP27B1 (cytochrome p450, family 27, subfamily B, polypeptide 1) and ALDH1a2 (aldehyde dehydrogenase 1 family, member A2) genes wherein the CYP27B1 is the gene for encoding 1α-hydroxylase and the ALDH1a2 is the gene for encoding RALDH2 can be constructed.

To construct the lentiviral vector, first the proper transgene plasmid constructs are prepared. To prepare the plasmid construct, 1.6 kb mouse CYP27B1 cDNA and RALDH2 can be amplified by PCR using a plasmid containing the mouse CYP27B1 and RALDH2 cDNA plasmids. The amplified mCYP27B1 cDNA fragment with a 5' KOZAK ribosome entry sequence can be cloned into the pRRL-SIN.cPPt.PGKGFP.WPRE lentiviral vector. The resulting construct is designated SFFV-CYP-PGK-GFP. The amplified mRALDH2 cDNA fragment can be cloned into the SFFV-CYP-PGK-GFP construct, and is named as SFFV-CYP-PGK-ALDH. This bicistronic plasmid expresses CYP27B1 controlled by the SFFV promoter and ALDH controlled by the nonspecific PGK promoter.

Once the transgene plasmid construct is prepared, HEK-293T cells can be transfected with the indicated transgene plasmid together with CMV VSVG and PAX2 plasmids in a calcium phosphate transfection solution that is made immediately before transfection. Supernatants are collected 48 hours after transient transfection. Viral particles can be concentrated by centrifugation for 24 hours at 6,000×g at 4° C. After removal of the supernatant, viral particles can be resuspended in phosphate-buffered saline (PBS) containing 5% glycerol and stored at −80° C. The biological titers were approximately $5 \times 10^7$ particles/mL as determined by FACS analysis of GFP+ cells in 293T cells transduced with various doses of the concentrated vectors.

Figure 2A:
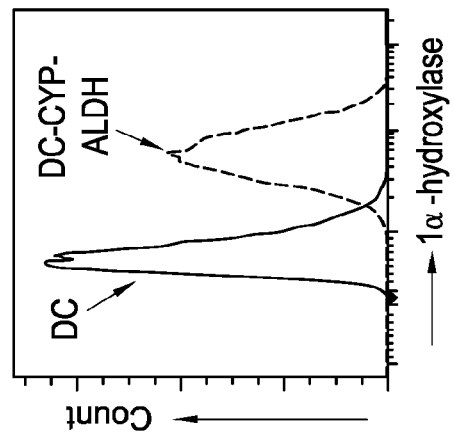
FIGS. 2A-2E depict the results of testing performed to engineer dendritic cells to constitutively overexpress 1α-hydroxylase and RALDH2.
Figure 2B:
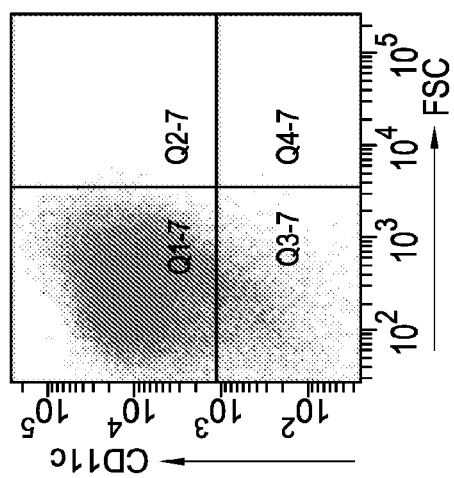
Figure 2C:
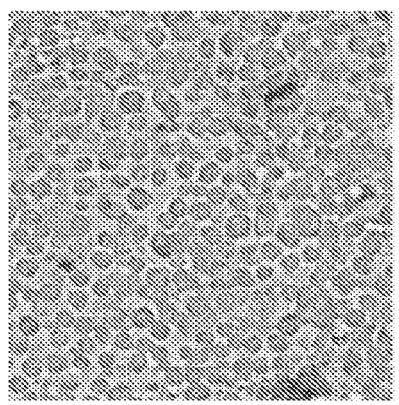
Figure 2D:
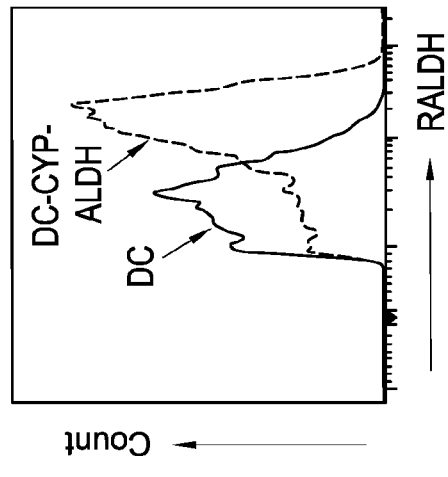
Figure 2E:
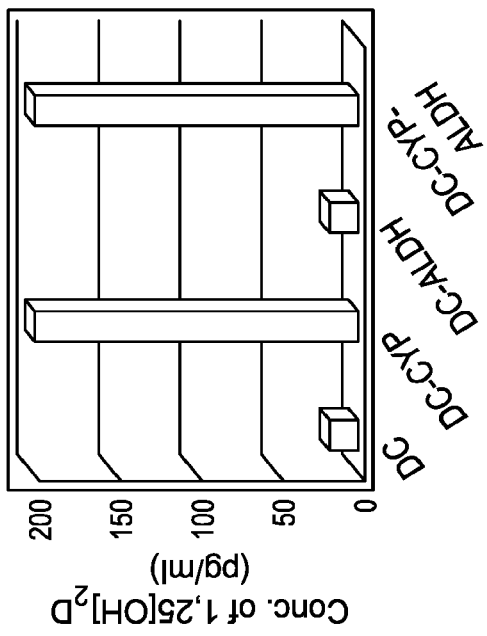

Subsequently, the viral vector can be packaged into viral particles that were used for transducing bone-marrow-derived DCs (BM-DCs). Cultured DCs displayed typical myeloid DC phenotype, i.e. protruding dendrites (FIG. 2A). In addition, more than 90% of the cultured DCs expressed DC11c, a DC marker (FIG. 2B). The DCs can be transduced with the lentiviral vector that expressed both CYP27B1 and ALDH1a2. In some embodiments, a lentiviral vector or other human applicable (e.g. AAV) vector can be used. These transduced DCs are referred as DC-CYP-ALDH. Following transduction, the DC-CYP-ALDH cells, as compared to wild type DCs (hereafter DC), showed significantly enhanced expression of 1α-hydroxylase as determined by flow cytometry as shown in FIG. 2C. A 1α-hydroxylase substrate, i.e. 25[OH]D (calcidiol) the major vitamin D form in the blood, can be added into cultured DCs. After overnight incubation, supernatants can be collected and the production of the active vitamin D metabolite $(1,25[OH]_2D)$ in the DC cultures can be measured to determine functional activity of the overexpressed 1α-hydroxylase. As shown in FIG. 2D, production of $1,25[OH]_2D$ was significantly increased (about 200×) in DC-CYP and DC-CYP-ALDH cell cultures, as compared to DC and DCALDH cell cultures. This indicates specific augmentation of 1α-hydroxylase activity in the DCs that were transduced with the CYP27B1-expressing viral vectors. To evaluate functional activity of the overexpressed RALDH2, a commercially produced non-toxic RALDH substrate, i.e. BODIPY™-aminoacetaldehyde (BAA), can be added into the DC cultures and the production of fluorescent product, i.e. BODIPYTMaminoacetate (BAA) can be measured by flow cytometry. The DC-CYP- ALDH cells, as compared to wild type DCs (DC), displayed significantly enhanced RALDH activity as analyzed using ALDEFLUOR assay as shown in FIG. 2E.

Figure 4:
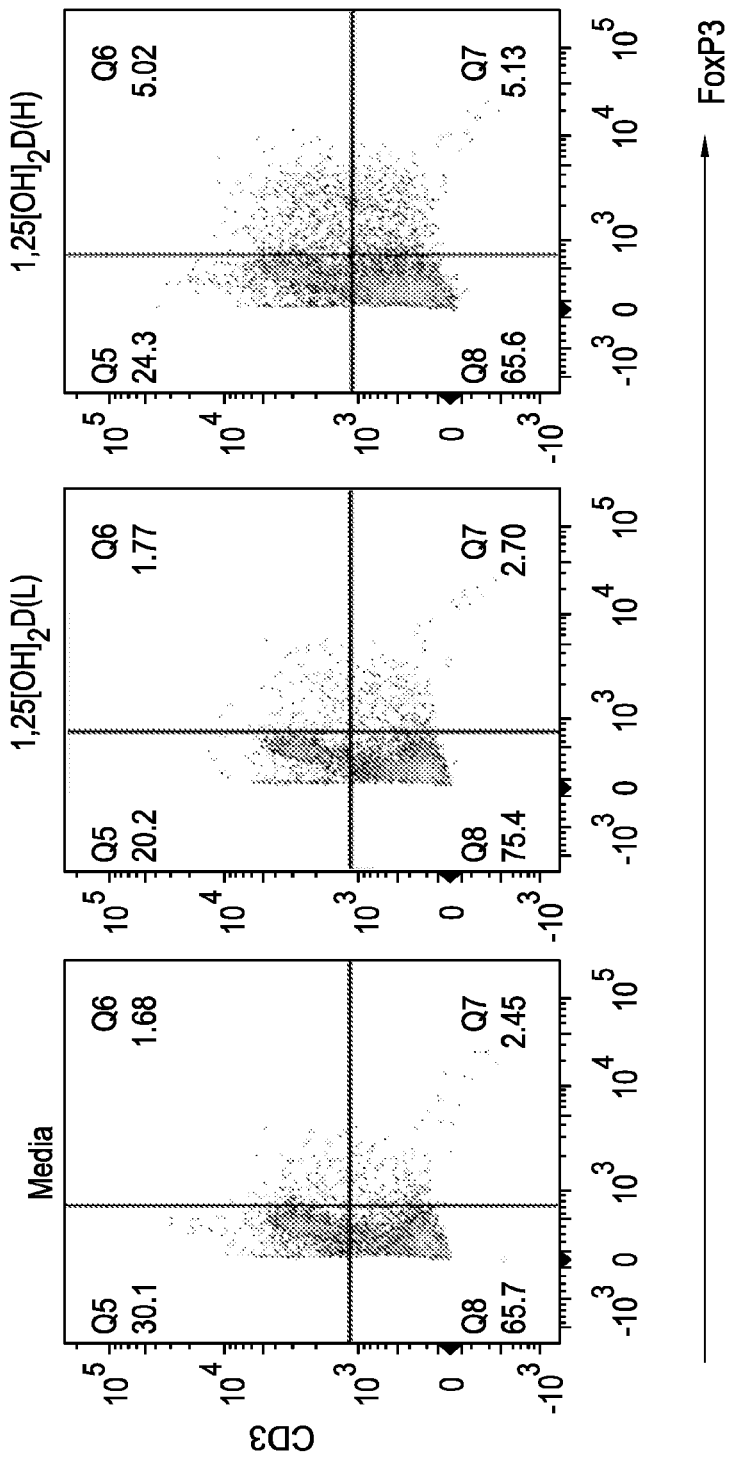
FIG. 4 depicts data from testing analyzing whether a high concentration of active vitamin D metabolite, 1,25[OH]$_2$D, is necessary for inducing foxp3$^+$ Treg cells in ex vivo cultures.

Example VII: Demonstration of Efficacy and Methods for the Necessity of a Supraphysiological Concentration of the Active Vitamin D Metabolite, 1,25[OH]$_2$D (Calcitriol), for Calcitriol to Induce Foxp3 Treg Cells in Ex Vivo Culture The efficacy of the disclosed agents and the methods was demonstrated as follows. A supraphysiological concentration of the active vitamin D metabolite, 1,25[OH]$_2$D (calcitriol), may be necessary for calcitriol to induce foxp3 expression during T cell priming. Foxp3 is a protein that is involved in the regulatory pathway in the development and function of regulatory T cells. To determine whether a supraphysiological concentration is necessary, foxp3 expression in T cells during T cell activation in the presence of exogenous calcitriol can be examined. Splenocytes can be activated by anti-CD3/CD28 magnetic beads. In some cultures, 1,25[OH]$_2$D can be added at a low (20 nM) or high (100 nM) concentration. Cells can be cultured for 72 hours and analyzed for foxp3 expression using flow cytometry. Flow cytometry can be performed by harvesting transduced mCYP27B1-positive DCs, washing them in PBS, resuspending them in the FACS buffer, and analyzing them for GFP expression on a flow cytometer. Although a low calcitriol concentration (20 nM) slightly up regulated foxp3 expression in activated T cells, a high calcitriol concentration (100 nM) was required to significantly augment foxp3 expression in the activated T cells as depicted by the data in FIG. 4. The normal range of human calcitriol serum concentration is 16~56 pg/ml (0.038 nM 0.13 nM). Although some patients may tolerate up to 300 pg/ml (0.72 nM) of serum calcitriol level without dose-limiting toxicity (i.e. hypercalcemia), this dose is far lower than the dose necessary for up regulation of foxp3 expression (20 nM) during T cell priming. Hence, this Treg inducing calcitriol dose is virtually impossible to reach through vitamin D and/or calcitriol supplementation because of the dose-limiting toxicity, which makes it necessary to engineer DCs with the 1α-hydroxylase so that an adequate concentration of calcitriol is available at immune synapses during T cell priming by DCs.

Example VIII: Demonstration of Efficacy of Agents and Methods for Immunization with Dendritic Cells Constitutively Overexpressing 1-Alpha-Hydroxylase and RALDH2 to Rapidly Arrest Progression of Ongoing Experimental Colitis The efficacy of the disclosed agents and the methods was demonstrated as follows. TNBS (2,4,6-trinitrobenzene sulfonic acid) colitis, which is mediated by a Th1 immune response and closely recapitulates human IBD pathology, can be induced in five to six week-old female C57BL/6 mice according to known methods. At day 3 after the disease induction, animals intravenously received different therapies [no treatment (No Tx), DC-CYP-ALDH, or DC-CYP). Mortality and body weights can be recorded daily. Although animals in the no treatment group had 100% mortality, animals in the DC-CYP-ALDH treatment group showed 0% mortality and animals in the DC-CYP treatment group had about 50% mortality (FIG. 3B). In addition, animals in the DC-CYP-ALDH treatment group rapidly gained body weight and survived. Animals in the DC-CYP treatment group also slowly gained body weight (FIG. 3B). On day 14, the animals were sacrificed.

The colons can be examined for length and by H&E staining as described below. Colon length in animals in the DC-CYP-ALDH treatment group was similar to healthy animals. Whereas animals in no treatment group displayed severely shortened colons, the colon length of animals in the DC-CYP treatment group was between the no treatment and DCCYP-ALDH treatment groups (FIG. 3C).

Finally, H&E staining analysis can be performed. After flushing with cold PBS, a segment of the distal colon can be fixed in 4% paraformaldehyde. A 10 µm-thick frozen section can be stained with H&E. These sections can then be examined blindly and scored by a pathologist. This method showed that colon tissues were severely damaged in animals in DC treatment group, while integrity of colon tissues in animals in the DC-CYP-ALDH treatment group was well maintained as compared to healthy animals as depicted in FIG. 3D. Hence the engineered DC-CYP-ALDH cells suppressed ongoing experimental colitis.

Figure 5A:
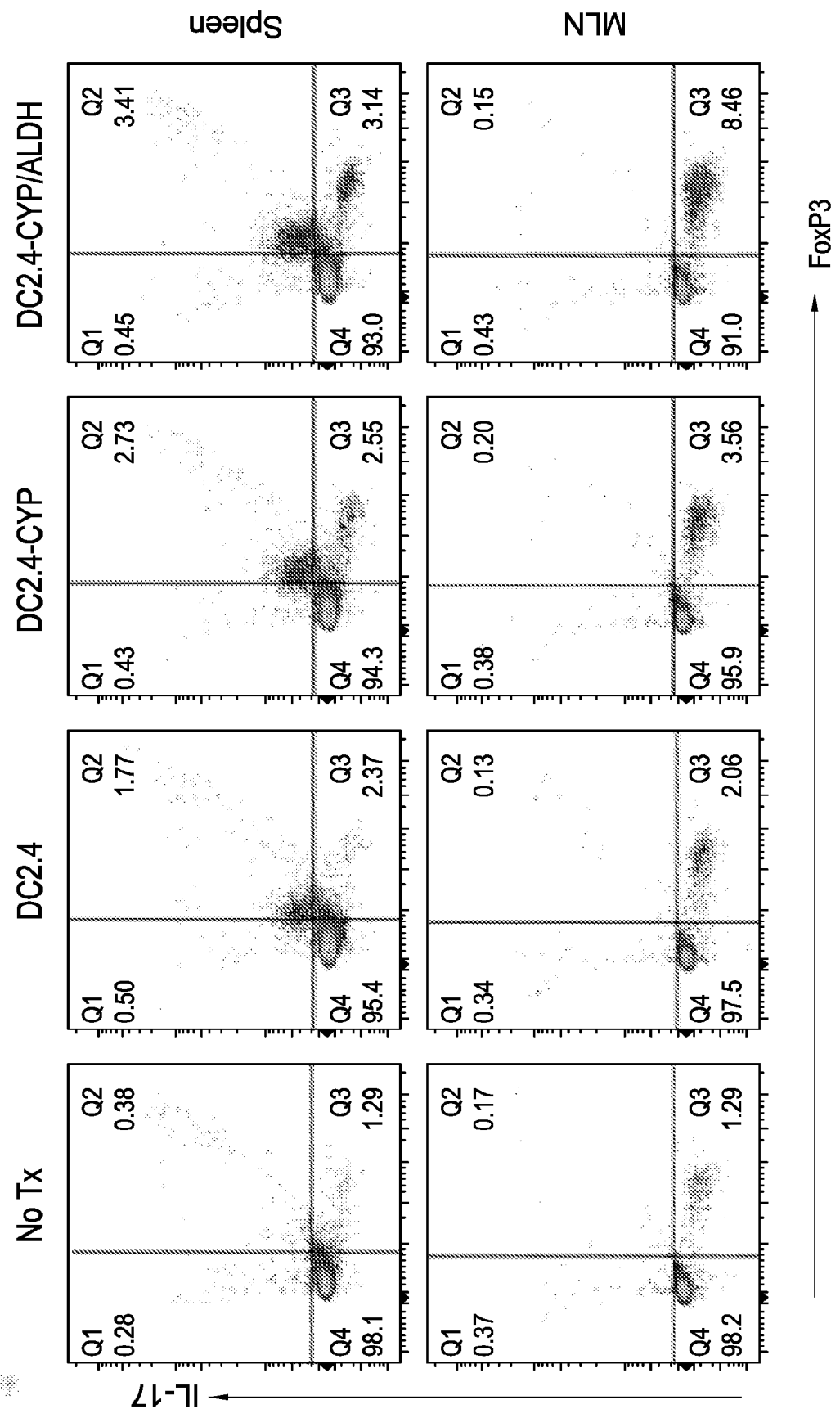
FIGS. 5A-C depicts data from testing analyzing the splenocytes of mice immunized with no treatment (No Tx), DC2.4, DC2.4-CYP, and DC2.4-CYP-ALDH cells for expression of fox3p, CCR9, IL-10, IL-14, and IL-2.
Figure 5B:
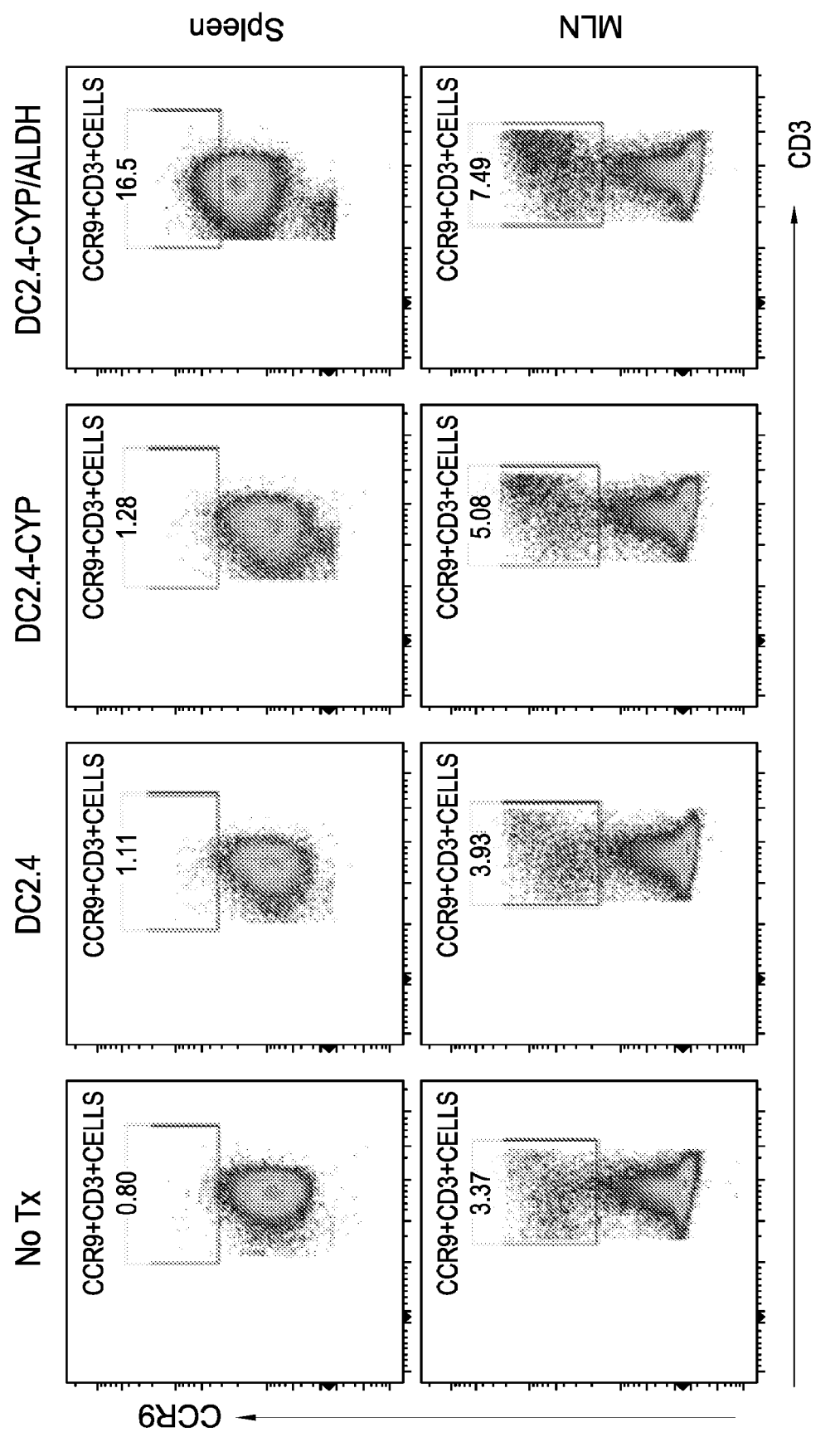
Figure 5C:
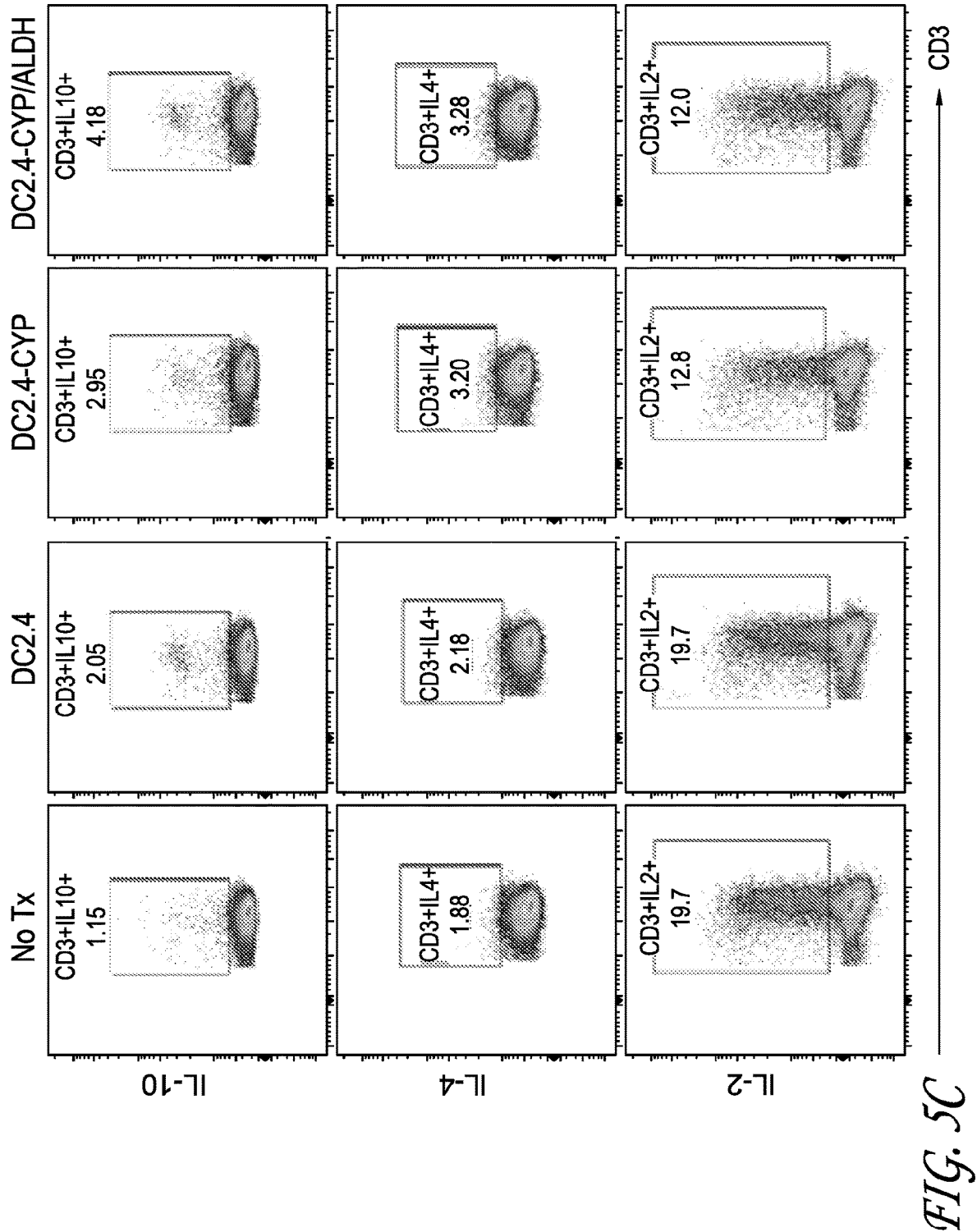

Example IX: Demonstration of Efficacy and Methods of Immunization with Dendritic Cells Engineered for Constitutive Overexpression of Both 1-Alpha-Hydroxylase and RALDH2 Enhances Expression of Foxp3, CCR9, IL-10, IL-4, but Decreases Expression of IL-2 in T Cells In Vivo The efficacy of the disclosed agents and the methods to induce Treg cells in vivo using DCs engineered for sufficient overexpression of 1α-hydroxylase and/or RALDH2 was demonstrated as follows. In some embodiments, the DCs can be bone-marrow- or PBMC (peripheral blood mononuclear cells)-derived dendritic cells that can be transduced with a vector thereby generating the gene-modified, lymphoid-tissue-homing dendritic cell. DC2.4 cells are a murine bone marrow-derived DC line from C57BL/6 mice. DC2.4 cells can be cultured in RPMI-1640 medium supplemented with 10% fetal bovine serum (FBS), 2 mM glutamine, 0.05 mM 2-mercaptoethanol and 100 µg/ml penicillin and streptomycin in 24 well plates in a humidified atmosphere containing 5% $CO_2$ at 37° C. Cell s are passaged at 80-90% confluence Two stable transgenic DC2.4 cell lines can be generated using the methods described in Example VI. One transgenic DC2.4 cell line carried constitutive overexpression of 1α-hydroxylase (DC2.4-CYP) and the other carried both 1α-hydroxylase and RALDH2 (DC2.4-CYP-ALDH). Balb/c mice can be intravenously immunized with the DC2.4, DC2.4-CYP, or DC2.4-CYP-ALDH, to induce an allogeneic response. Animals that did not receive any treatment can be included as controls. The mice were sacrificed ten days after the immunization. T cells in splenocytes and mesenteric lymph nodes of the animals can be examined for expressions of foxp3$^+$, CCR9, IL-10, IL-4, IL-2, and IL-17 by multichromatic flow cytometry as described in Example VII. The results are shown in FIGS. 5A-5C. The data showed that, although DC2.4-CYP cells had similar effects, DC2.4-CYP-ALDH cells among different treatments induced the strongest expression of foxp3, CCR9, and IL-10 in T cells from both spleens and mesenteric lymph nodes, suggesting induction of gut-homing Treg cells in the peripheral lymphoid tissues. IL-17$^+$/foxp3$^+$ double positive T cells were consistently observed in the spleens of the immunized animals (FIG. 5A). The IL-17$^+$/foxp3$^+$ T cells have been observed in both animals and humans to possess suppressive activity. In addition, a slightly increased IL-4 and decreased IL-2 expressions were also evident in animals treated with the DC2.4-CYP and DC2.4-CYP-ALDH cells. The above observations suggest that DC-CYP-ALDH therapy is able to significantly increase generation of gut-homing Treg cells in the peripheral lymphoid tissues.

Figure 6A:
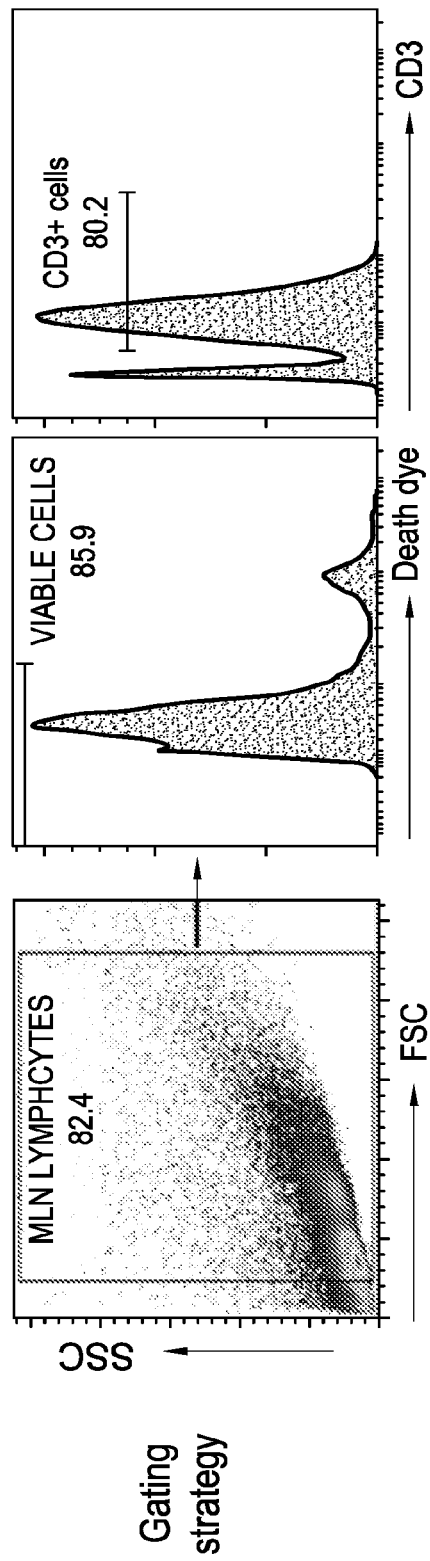
FIG. 6A depicts a gating strategy for a test to determine whether administered DC-CYP-ALDH cells increase foxp3$^+$ Treg cells in the inflamed GUT in vivo.
Figure 6B:
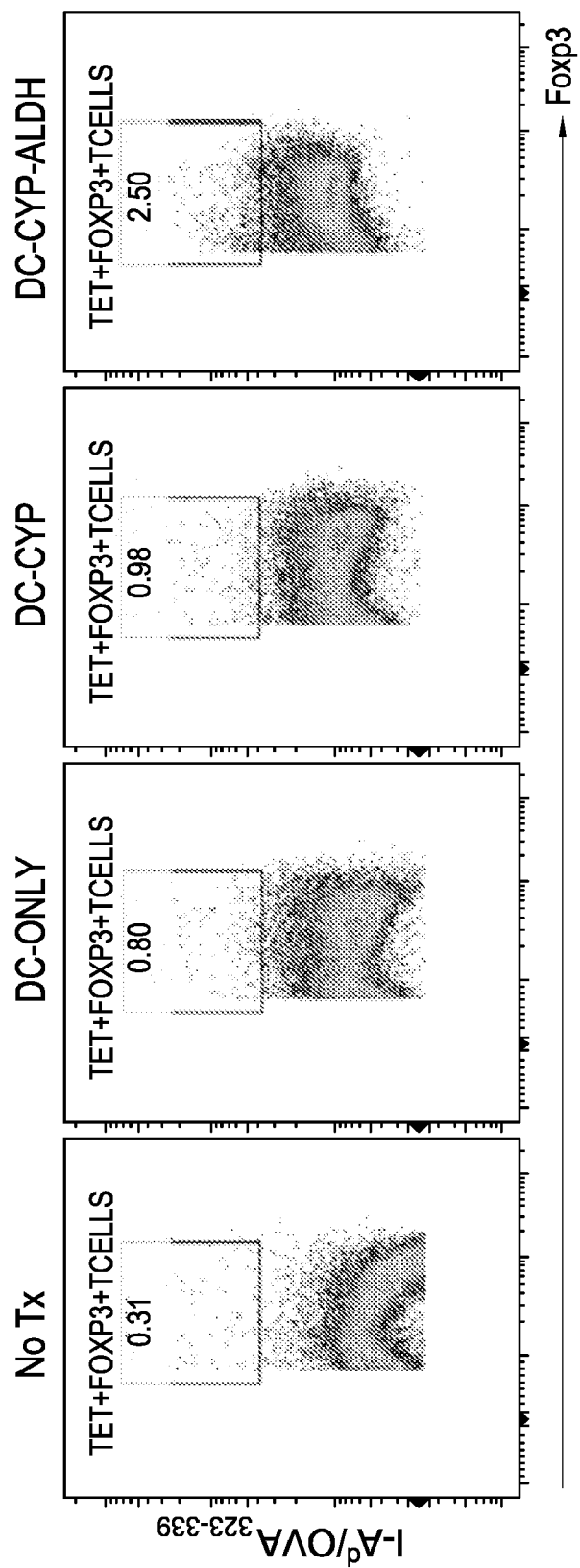
FIG. 6B is a representative FACS plots from a test run using the gating strategy of FIG. 6A for mice immunized with no treatment (No Tx) or OVA$_{323-339}$-pulsed DC, DC-CYP, or DC-CYP-ALDH cells, analyzing the number of OVA$_{323-339}$/I-A$^d$ tetramer$^+$ cells among the foxp3$^+$ Tcells in colon tissues.

Example X: Demonstration of Efficacy and Methods of Immunization with Dendritic Cells Engineered for Constitutive Overexpression of Both 1-Alpha-Hydroxylase and RALDH2 Enhances Migration of Antigen-Specific Foxp3+ Treg Cells, Generated in Draining Lymph Nodes, into Intestines The efficacy of the disclosed agents and the methods was demonstrated as follows. Data depicted in FIGS. 5A-5C suggests that DC-CYP-ALDH cells are able to strongly increase generation of gut-homing Treg cells in peripheral lymphoid tissues. Therefore, the Treg cells in the intestines should be increased in the immunized animals. To test this, Balb/c mice can be subcutaneously immunized with $OVA_{323-33}$-pulsed DCs at days 0 and 10. A group of mice that did not receive any treatment can be included as controls. Ten days after the second immunization, the mice were sacrificed. Colon tissues from the mice can be analyzed for $OVA_{323-339}/I-A^d$ tetramers. The presence of $OVA_{323-339}/I-A^d$ tetramers among the fox3p$^+$ T cells indicates migration of the $OVA_{323-339}$-specific Treg cells from local draining lymph nodes into the intestines. Animals subcutaneously immunized with $OVA_{323-339}$-pulsed DC-CYP-ALDH, but not DC and DC-CYP, showed significantly increased $OVA_{323-339}/I-A^d$ tetramer$^+$ cells among foxp3$^+$ Treg cells in colons as shown in FIGS. 6A-6B. The data demonstrate that overexpression of RA in the DCs is necessary for promoting migration of the Treg cells, generated in peripheral lymphoid tissues, into intestines.

Figure 7:
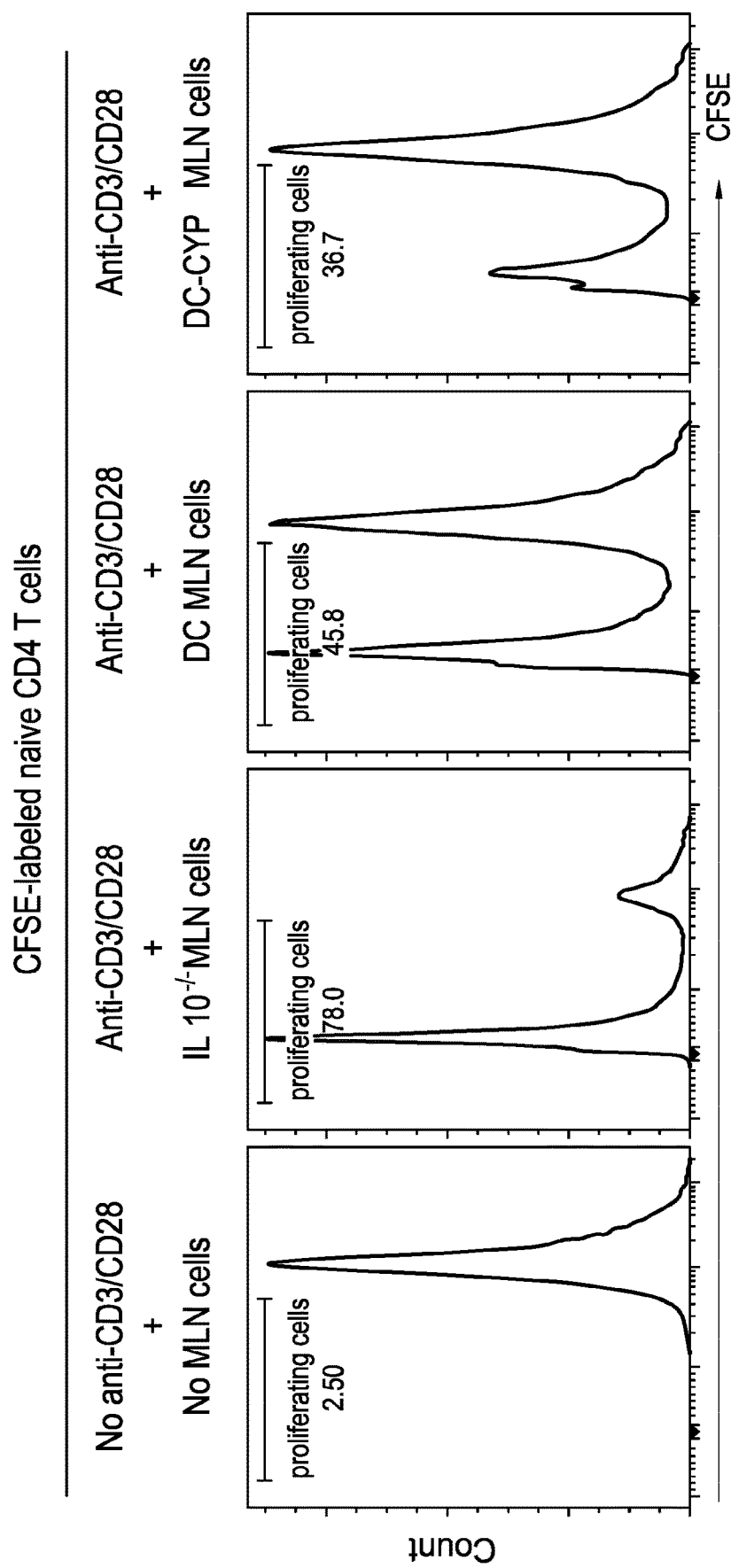
FIG. 7 depicts the results of testing performed to determine whether DC-CYP-ALDH cells enhance GUT-associated immunoregulatory functions in vivo.

Example XI: Demonstration of Efficacy and Methods of Immunization with Dendritic Cells Engineered for Constitutive Overexpression of 1-Alpha-Hydroxylase Enhances Immune Regulatory Activity in the Peripheral Lymphoid Tissue In Vivo The efficacy of the disclosed agents and the methods was demonstrated as follows. Because DC-CYP immunization alone, although to a lesser degree as compared to DC-CYP-ALDH, can increase expression of foxp3 and IL-10 especially in MLN T cells (FIGS. 5A-5C and Example IX), testing can be performed to address whether regulatory activity of the mononuclear cells (MNCs) in MLNs could be augmented by DC-CYP immunization. Balb/c mice were subcutaneously immunized with non-engineered DCs (DC) or DC-CYP at days 0 and 10 using the methods described above. A group of non-immunized mice can be included as a control. Ten days after the second immunization, the mice were sacrificed. Mononuclear cells (MNCs) in mesenteric lymph nodes (MLN) can be evaluated for ability to suppress proliferation of CFSE-labeled syngeneic naive CD4$^+$ T cells using the following method. The MNCs of the MLN from the immunized mice can be co-cultured with CFSE-labeled naive CD4$^+$ T cells at 1:1 ratio. In addition, IL-10$^{-/-}$ MLN MNCs can be included as a negative control. The data show that MLN MNCs from IL-10$^{-/-}$ mice lacked suppressive activity as shown in FIG. 7 (78% of the CD4$^+$ T cells proliferated), which is consistent with spontaneous development of colitis in the IL-10$^{-/-}$ animals. However, MLN MNCs from DC-CYP (53% suppression versus IL-10$^{-/-}$ MLN MNC), as compared DC (41% suppression versus IL10$^{-/-}$ MLN MNC) immunized mice showed stronger suppressive activity. Therefore, the data demonstrate that DC-CYP immunization is indeed able to augment regulatory activity in the peripheral lymphoid tissues.

Although the present disclosure has been discussed in considerable detail with reference to certain preferred embodiments, other embodiments are possible. Therefore, the scope of the appended claims should not be limited to the description of preferred embodiments contained in this disclosure.

A "patient" as used herein may refer to a human or a non-human mammal, e.g., a dog, a cat, a mouse, a rat, a cow, a sheep, a pig, a goat, a non-human primate or a bird, e.g., a chicken, as well as any other vertebrate or invertebrate.

An "effective amount" or a "therapeutically effective amount" as used herein refers to an amount of a therapeutic agent that is effective to relieve, to some extent, or to reduce the likelihood of onset of, one or more of the symptoms of a disease or condition (e.g., neuropathic pain), and includes curing the disease or condition. A prophylactically effective amount as used herein refers to an amount that is effective to prevent or delay the onset of one or more symptoms of a disease or condition (e.g., neuropathic pain), or otherwise reduce the severity of said one or more symptoms, when administered to a subject who does not yet exhibit symptoms of a disease or condition, but who is susceptible to, or otherwise at risk of, a particular disease or condition.

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration.

In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Some embodiments include the combination of compounds, therapeutic agents, and/or pharmaceutical compositions described herein. In such embodiments, the two or more agents may be administered at the same time or substantially the same time. In other embodiments, the two or more agents are administered sequentially. In some embodiments, the agents are administered through the same route (e.g. orally) and in yet other embodiments, the agents are administered through different routes (e.g. one agent is administered orally while another agent is administered intravenously).

That claimed is:

1. A gene-modified dendritic cell for treating a gastrointestinal inflammatory disease, the gene-modified dendritic cell overexpressing a cytochrome p450 family 27 subfamily B polypeptide 1 (CYP27B1) gene encoding 1-alpha-hydroxylase and overexpressing an aldehyde dehydrogenase 1 family member A2 (ALDH1a2) gene encoding retinaldehyde dehydrogenase 2 (RALDH2), wherein the gene-modified dendritic cell is engineered to constitutively overexpress the 1-alpha-hydroxylase.

2. The gene-modified dendritic cell of claim 1, wherein the gene-modified dendritic cell is engineered to constitutively overexpress the RALDH2.

3. The gene-modified dendritic cell of claim 1, wherein the gene-modified dendritic cell is engineered to constitutively overexpress both the 1-alpha-hydroxylase and the RALDH2.

4. The gene-modified dendritic cell of claim 1, wherein the gene-modified dendritic cell is derived from a bone marrow or a peripheral blood mononuclear cell (PBMC).

5. The gene-modified dendritic cell of claim 3, wherein the gene-modified dendritic cell is derived from a bone marrow or a peripheral blood mononuclear cell (PBMC).

6. The gene-modified dendritic cell of claim 1, wherein the gene-modified dendritic cell contains a bicistronic expression vector with a spleen focus-forming viral (SFFV) promoter controlling the expression of the CYP27B1 gene and a phosphoglycerate kinase (PGK) promoter controlling the expression of the ALDH1a2 gene.

7. The gene-modified dendritic cell of claim 6, wherein the vector is derived from a lentivirus.

8. The gene-modified dendritic cell of claim 6, wherein the vector is derived from an adeno-associated virus.

9. A pharmaceutical composition comprising the gene-modified dendritic cell of claim 1 and a pharmaceutically acceptable carrier.

10. The gene-modified dendritic cell of claim 1, wherein the gene-modified dendritic cell comprises a first expression vector comprising a first nucleic acid sequence comprising a sequence of a CYP27B1 gene but not an ALDH1a2 gene and an operably linked promoter or a second expression vector comprising a second nucleic acid sequence comprising a sequence of an ALDH1a2 gene but not a CYP27B1 gene and an operably linked promoter.

* * * * *